US012671747B2

(12) United States Patent
Ragelhassi et al.

(10) Patent No.: US 12,671,747 B2
(45) Date of Patent: Jun. 30, 2026

(54) DEVICE, SYSTEM, AND METHOD FOR SECURE ACCESS TO VIRTUAL PLATFORMS

(71) Applicant: AMADEUS S.A.S., Biot (FR)

(72) Inventors: Habib Ragelhassi, Biot (FR);
Ghislaine Bel Genovesi, Biot (FR);
Rodolphe Texier, Biot (FR)

(73) Assignee: AMADEUS S.A.S., Biot (FR)

( * ) Notice: Subject to any disclaimer, the term of this patent is extended or adjusted under 35 U.S.C. 154(b) by 34 days.

(21) Appl. No.: 18/807,282

(22) Filed: Aug. 16, 2024

(65) Prior Publication Data

US 2025/0063095 A1      Feb. 20, 2025

(30) Foreign Application Priority Data

Aug. 17, 2023     (EP) ..................................... 23315319

(51) Int. Cl.
H04L 67/50          (2022.01)
G06T 15/00          (2011.01)
G16H 10/60          (2018.01)

(52) U.S. Cl.
CPC ............ H04L 67/50 (2022.05); G06T 15/005 (2013.01); G16H 10/60 (2018.01)

(58) Field of Classification Search
None
See application file for complete search history.

(56) References Cited

U.S. PATENT DOCUMENTS

| | | | | |
|---|---|---|---|---|
| 8,612,363 B2 * | 12/2013 | Karkanias | .............. | G16H 40/67 706/11 |
| 9,830,423 B2 * | 11/2017 | Biswas | .................. | G16H 40/67 |
| 11,615,600 B1 | 3/2023 | Morgan et al. | | |
| 11,961,197 B1 * | 4/2024 | Morgan | ................. | G16H 20/00 |

(Continued)

OTHER PUBLICATIONS

Zhang, Kexin, et al.,"It's Just Part of Me: Understanding Avatar Diversity and Self-presentation of People with Disabilities in Social Virtual Reality"—Proceedings of the Seventeenth European Conference on Computer Systems, ACMPUB 27, New York, NY, USA, Oct. 23, 2022 pp. 1-16, XP058914191.

(Continued)

*Primary Examiner* — Ranodhi Serrao
(74) *Attorney, Agent, or Firm* — PERRY + CURRIER INC.

(57) ABSTRACT

A device, system and method for secure access to virtual platforms is provided. A computing device establishes a communication session between a client device and a virtual platform, the client device configured to provide rendered scenes of the virtual platform based on scene rendering data generated by the virtual platform. The computing devices accesses disability compensation data indicative of how to compensate for a disability associated with a user of the client device, the disability compensation data anonymized to remove personal identifiable information associated with the user. The computing device adjusts settings of the virtual platform according to the disability compensation data to control the virtual platform to generate the scene rendering data according to the settings as adjusted, such that the client device renders scenes of the virtual platform to replicate the disability for an avatar associated with the user in the virtual platform.

20 Claims, 9 Drawing Sheets

(56) References Cited

U.S. PATENT DOCUMENTS

| | | | |
|---|---|---|---|
| 2009/0309891 A1* | 12/2009 | Karkanias | A63F 13/65 345/581 |
| 2013/0241719 A1* | 9/2013 | Biswas | G16H 10/60 340/407.1 |
| 2016/0294793 A1* | 10/2016 | Larson | H04L 63/1408 |
| 2017/0080346 A1* | 3/2017 | Abbas | A63F 13/79 |
| 2018/0082028 A1* | 3/2018 | Davey | G16H 10/60 |
| 2020/0356136 A1 | 11/2020 | Aimone et al. | |
| 2020/0372713 A1 | 11/2020 | Hewitt et al. | |
| 2021/0240720 A1 | 8/2021 | Muse et al. | |
| 2023/0284915 A1* | 9/2023 | Soori-Arachi | A61B 5/6898 |
| 2025/0005966 A1* | 1/2025 | Soori-Arachi | G06V 40/18 |

OTHER PUBLICATIONS

Mircea, Maria-Madalina, et al, "A Machine Learning Approach for Data Protection in Virtually Reality Therapy Applications", 2021 IEEE 17th International Conference on Intelligent Computer Communication and Processing (ICCP), IEEE, Oct. 28, 2021, pp. 367-374, XP034102752.
Gerling, Kathrin, et al., "Virtual Reality Games for People Using Wheelchairs", Proceedings of the Genetic and Evolutionary Computation Confrence, ACMPUB 27, New York, NY, USA, Apr. 21, 2020, pp. 1-11 XP058550586.
"Extended European Search Report", mailed Feb. 20, 2024, issued in the corresponding European patent application No. 23315319.6, Filed Aug. 17, 2023.

\* cited by examiner

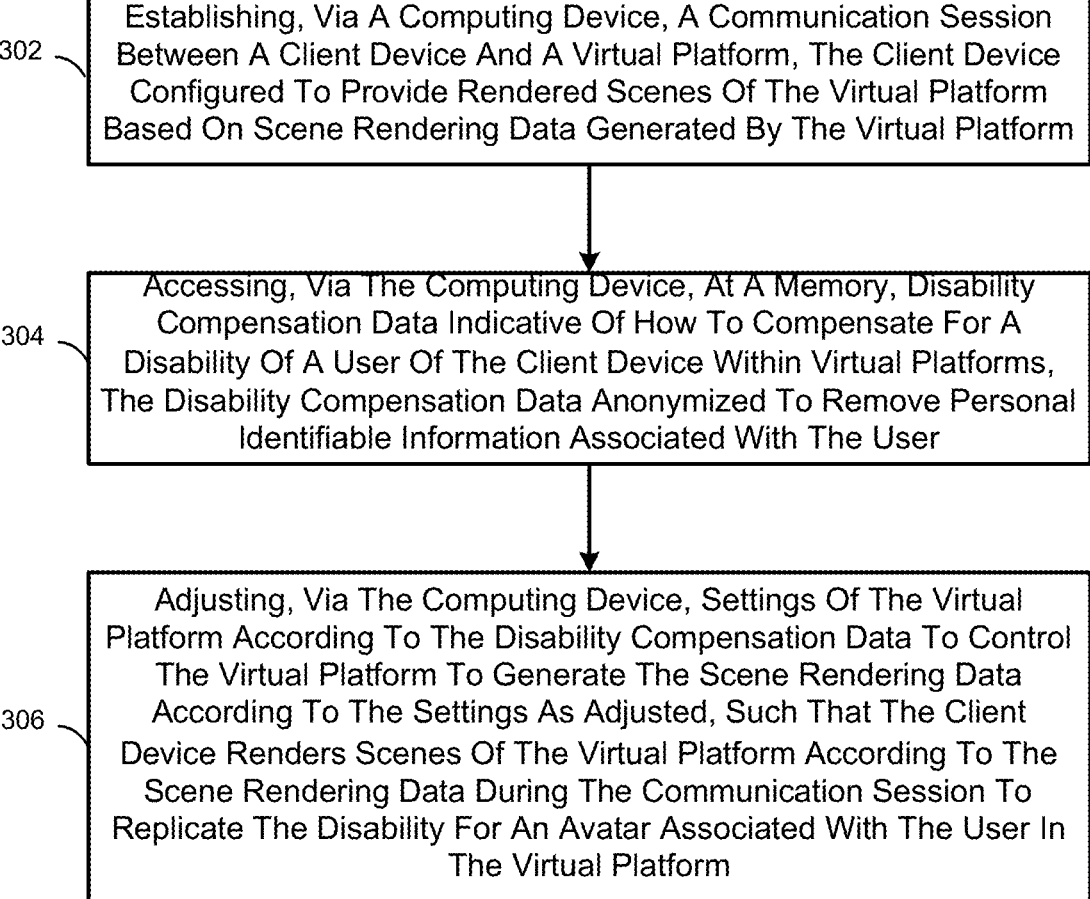

302 — Establishing, Via A Computing Device, A Communication Session Between A Client Device And A Virtual Platform, The Client Device Configured To Provide Rendered Scenes Of The Virtual Platform Based On Scene Rendering Data Generated By The Virtual Platform 304 — Accessing, Via The Computing Device, At A Memory, Disability Compensation Data Indicative Of How To Compensate For A Disability Of A User Of The Client Device Within Virtual Platforms, The Disability Compensation Data Anonymized To Remove Personal Identifiable Information Associated With The User 306 — Adjusting, Via The Computing Device, Settings Of The Virtual Platform According To The Disability Compensation Data To Control The Virtual Platform To Generate The Scene Rendering Data According To The Settings As Adjusted, Such That The Client Device Renders Scenes Of The Virtual Platform According To The Scene Rendering Data During The Communication Session To Replicate The Disability For An Avatar Associated With The User In The Virtual Platform

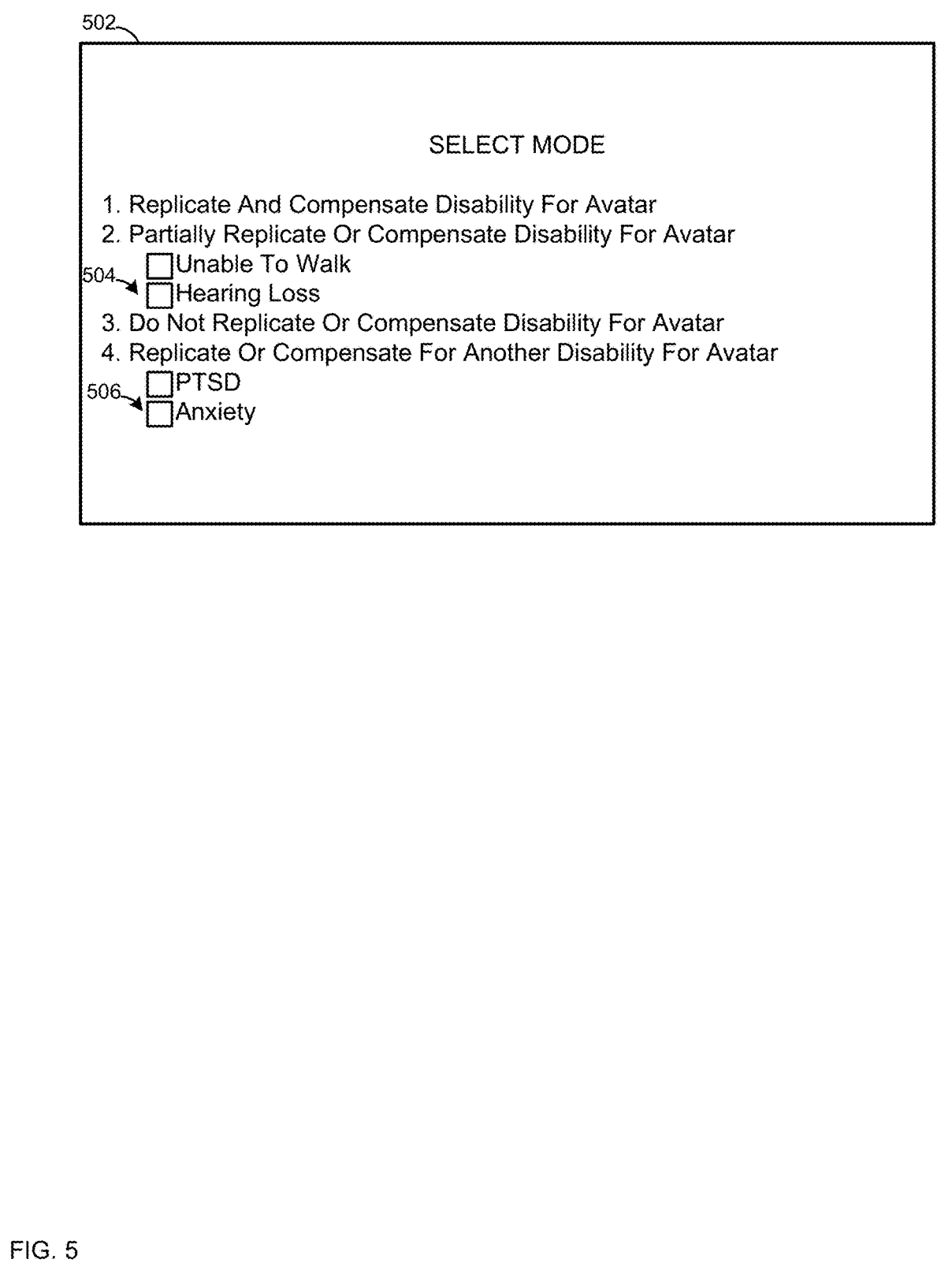

SELECT MODE

1. Replicate And Compensate Disability For Avatar
2. Partially Replicate Or Compensate Disability For Avatar
504 ☐ Unable To Walk
☐ Hearing Loss
3. Do Not Replicate Or Compensate Disability For Avatar
4. Replicate Or Compensate For Another Disability For Avatar
506 ☐ PTSD
☐ Anxiety

FIG. 5

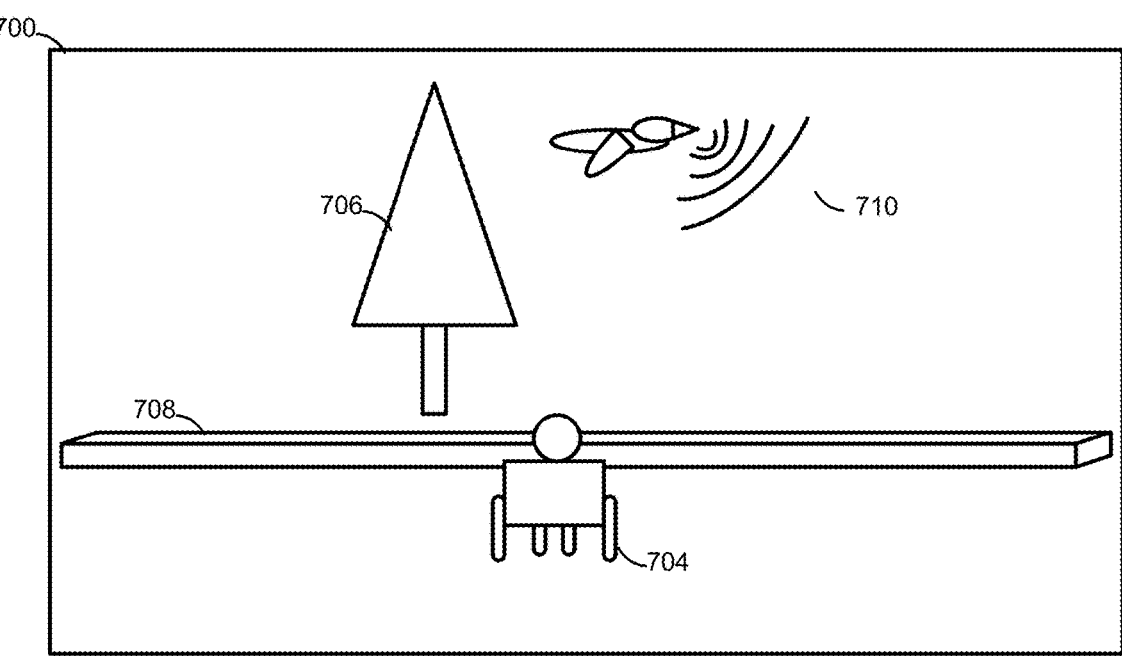
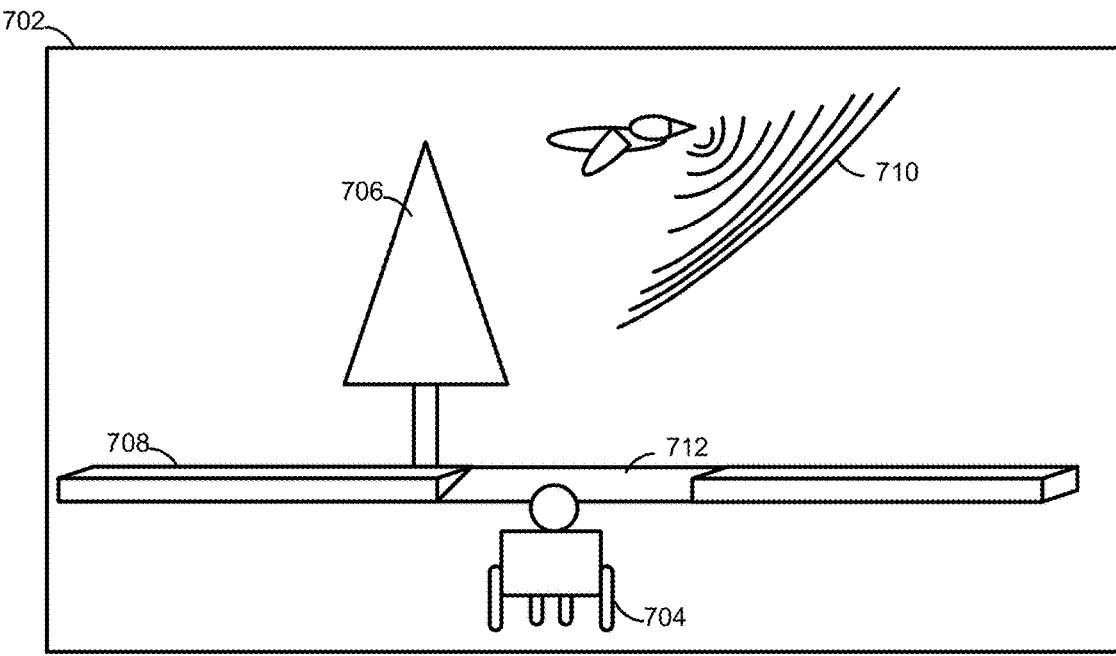
FIG. 7

DEVICE, SYSTEM, AND METHOD FOR SECURE ACCESS TO VIRTUAL PLATFORMS

FIELD

The present specification relates generally to internet security, and specifically to a device, system and method for secure access to virtual platforms.

BACKGROUND

Users with disabilities may interact with virtual platforms, such as augmented reality and/or virtual reality platforms, which may provide augmented reality and/or virtual reality environments. However, they may prefer to do so without disclosing their disability to the virtual platform, as this may lead to privacy breaches.

SUMMARY

A first aspect of the present specification provides a method comprising: establishing, via a computing device, a communication session between a client device and a virtual platform, the client device configured to provide rendered scenes of the virtual platform based on scene rendering data generated by the virtual platform; accessing, via the computing device, at a memory, disability compensation data indicative of how to compensate for a disability associated with a user of the client device within virtual platforms, the disability compensation data anonymized to remove personal identifiable information associated with the user; and adjusting, via the computing device, settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform.

The method of the first aspect may further comprise: receiving biometric data associated with the user during the communication session; and further adjusting the settings of the virtual platform based on the biometric data.

The method of the first aspect may further comprise: receiving biometric data associated with the user during the communication session; and adjusting the disability compensation data based on the biometric data.

The method of the first aspect may further comprise: accessing medical records associated with the user; generating the disability compensation data from the medical records including removing any of the personal identifiable information in the medical records from the disability compensation data; and deleting copies of the medical records generated when accessing the medical records and generating the disability compensation data.

At the method of the first aspect, the disability compensation data may comprise: specific indications for adjusting the settings of the virtual platform to compensate for the disability, the specific indications including specific settings adjustments.

At the method of the first aspect, the disability compensation data may comprise: generic indications for adjusting the settings of the virtual platform to compensate for the disability, the generic indications omitting specific settings adjustments, and the adjusting the settings of the virtual platform according to the disability compensation data may comprise: translating the generic indications for adjusting the settings into specific setting adjustments to the settings.

At the method of the first aspect, the disability compensation data may omit any reference to a type of the disability.

The method of the first aspect may further comprise: receiving, from the client device, an indication to adjust the settings of the virtual platform; and adjusting the settings based on the indication, wherein the indication may comprise one of: a first indication to replicate, or compensate for, the disability for the avatar associated with the user in the virtual platform; a second indication to partially replicate, or partially compensate for, the disability for the avatar in the virtual platform; a third indication to stop replicating, or not compensate for, the disability for the avatar in the virtual platform; and a fourth indication to simulate, or compensate for, a given disability for the avatar in the virtual platform.

The method of the first aspect may further comprise: causing an assistive device, used by the user of the client device, to adjust, to one or more of alleviate and avoid one or more disabilities of the user of the client device.

A second aspect of the present specification provides a computing device comprising: a controller; and a computer-readable storage medium having stored thereon program instructions that, when executed by the controller, cause the computing device to perform a set of operations comprising: establishing a communication session between a client device and a virtual platform, the client device configured to provide rendered scenes of the virtual platform based on scene rendering data generated by the virtual platform; accessing, at a memory, disability compensation data indicative of how to compensate for a disability associated with a user of the client device within virtual platforms, the disability compensation data anonymized to remove personal identifiable information associated with the user; and adjusting settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform.

At the computing device of the second aspect, the set of operations may further comprise: receiving biometric data associated with the user during the communication session; and further adjusting the settings of the virtual platform based on the biometric data.

At the computing device of the second aspect, the set of operations may further comprise: receiving biometric data associated with the user during the communication session; and adjusting the disability compensation data based on the biometric data.

At the computing device of the second aspect, the set of operations may further comprise: accessing medical records associated with the user; generating the disability compensation data from the medical records including removing any of the personal identifiable information in the medical records from the disability compensation data; and deleting copies of the medical records generated when accessing the medical records and generating the disability compensation data.

At the computing device of the second aspect, the disability compensation data may comprise: specific indications for adjusting the settings of the virtual platform to compensate for the disability, the specific indications including specific settings adjustments.

At the computing device of the second aspect, the disability compensation data may comprise: generic indications for adjusting the settings of the virtual platform to compensate for the disability, the generic indications omitting specific settings adjustments, and the adjusting the settings of the virtual platform according to the disability compensation data may comprise: translating the generic indications for adjusting the settings into specific setting adjustments to the settings.

At the computing device of the second aspect, the disability compensation data may omit any reference to a type of the disability.

At the computing device of the second aspect, the set of operations may further comprise: receiving, from the client device, an indication to adjust the settings of the virtual platform; and adjusting the settings based on the indication, wherein the indication may comprise one of: a first indication to replicate, or compensate for, the disability for the avatar associated with the user in the virtual platform; a second indication to partially replicate, or partially compensate for, the disability for the avatar in the virtual platform; a third indication to stop replicating, or not compensate for, the disability for the avatar in the virtual platform; and a fourth indication to simulate, or compensate for, a given disability for the avatar in the virtual platform.

At the computing device of the second aspect, the set of operations may further comprise: causing an assistive device, used by the user of the client device, to adjust, to one or more of alleviate and avoid one or more disabilities of the user of the client device.

A third aspect of the present specification provides a non-transitory computer-readable storage medium having stored thereon program instructions that, when executed by a computing device, causes the computing device to perform a method comprising: establishing a communication session between a client device and a virtual platform, the client device configured to provide rendered scenes of the virtual platform based on scene rendering data generated by the virtual platform; accessing at a memory, disability compensation data indicative of how to compensate for a disability associated with a user of the client device within virtual platforms, the disability compensation data anonymized to remove personal identifiable information associated with the user; and adjusting settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform.

The method of the third aspect may further comprise: receiving biometric data associated with the user during the communication session; and further adjusting the settings of the virtual platform based on the biometric data.

The method of the third aspect may further comprise: receiving biometric data associated with the user during the communication session; and adjusting the disability compensation data based on the biometric data.

The method of the third aspect may further comprise: accessing medical records associated with the user; generating the disability compensation data from the medical records including removing any of the personal identifiable information in the medical records from the disability compensation data; and deleting copies of the medical records generated when accessing the medical records and generating the disability compensation data.

At the method of the third aspect, the disability compensation data may comprise: specific indications for adjusting the settings of the virtual platform to compensate for the disability, the specific indications including specific settings adjustments.

At the method of the third aspect, the disability compensation data may comprise: generic indications for adjusting the settings of the virtual platform to compensate for the disability, the generic indications omitting specific settings adjustments, and the adjusting the settings of the virtual platform according to the disability compensation data may comprise: translating the generic indications for adjusting the settings into specific setting adjustments to the settings.

At the method of the third aspect, the disability compensation data may omit any reference to a type of the disability.

The method of the third aspect may further comprise: receiving, from the client device, an indication to adjust the settings of the virtual platform; and adjusting the settings based on the indication, wherein the indication may comprise one of: a first indication to replicate, or compensate for, the disability for the avatar associated with the user in the virtual platform; a second indication to partially replicate, or partially compensate for, the disability for the avatar in the virtual platform; a third indication to stop replicating, or not compensate for, the disability for the avatar in the virtual platform; and a fourth indication to simulate, or compensate for, a given disability for the avatar in the virtual platform.

The method of the third aspect may further comprise: causing an assistive device, used by the user of the client device, to adjust, to one or more of alleviate and avoid one or more disabilities of the user of the client device.

BRIEF DESCRIPTIONS OF THE DRAWINGS

For a better understanding of the various examples described herein and to show more clearly how they may be carried into effect, reference will now be made, by way of example only, to the accompanying drawings in which:

FIG. 3 depicts a flowchart of a method for secure access to virtual platforms, according to non-limiting examples.

FIG. 5 depicts an example of a graphic user interface for selecting a mode in the system of FIG. 1, according to non-limiting examples.

FIG. 7 depicts examples of rendered scenes before and after implementing aspects of a method for secure access to virtual platforms, according to non-limiting examples.

DETAILED DESCRIPTION

Users with disabilities may interact with virtual platforms, such as augmented reality and/or virtual reality platforms, which may provide augmented reality and/or virtual reality environments. However, they may prefer to do so without disclosing their disability to the virtual platform, as this may lead to privacy breaches. For example, the users may want to experience a virtual platform via a client device, such as a virtual reality headset, but doing so may lead to sharing of personal identifiable information with the virtual platform, which may be insecure. As such, provided herein is a device, system and method for secure access to virtual platforms.

Figure 1:
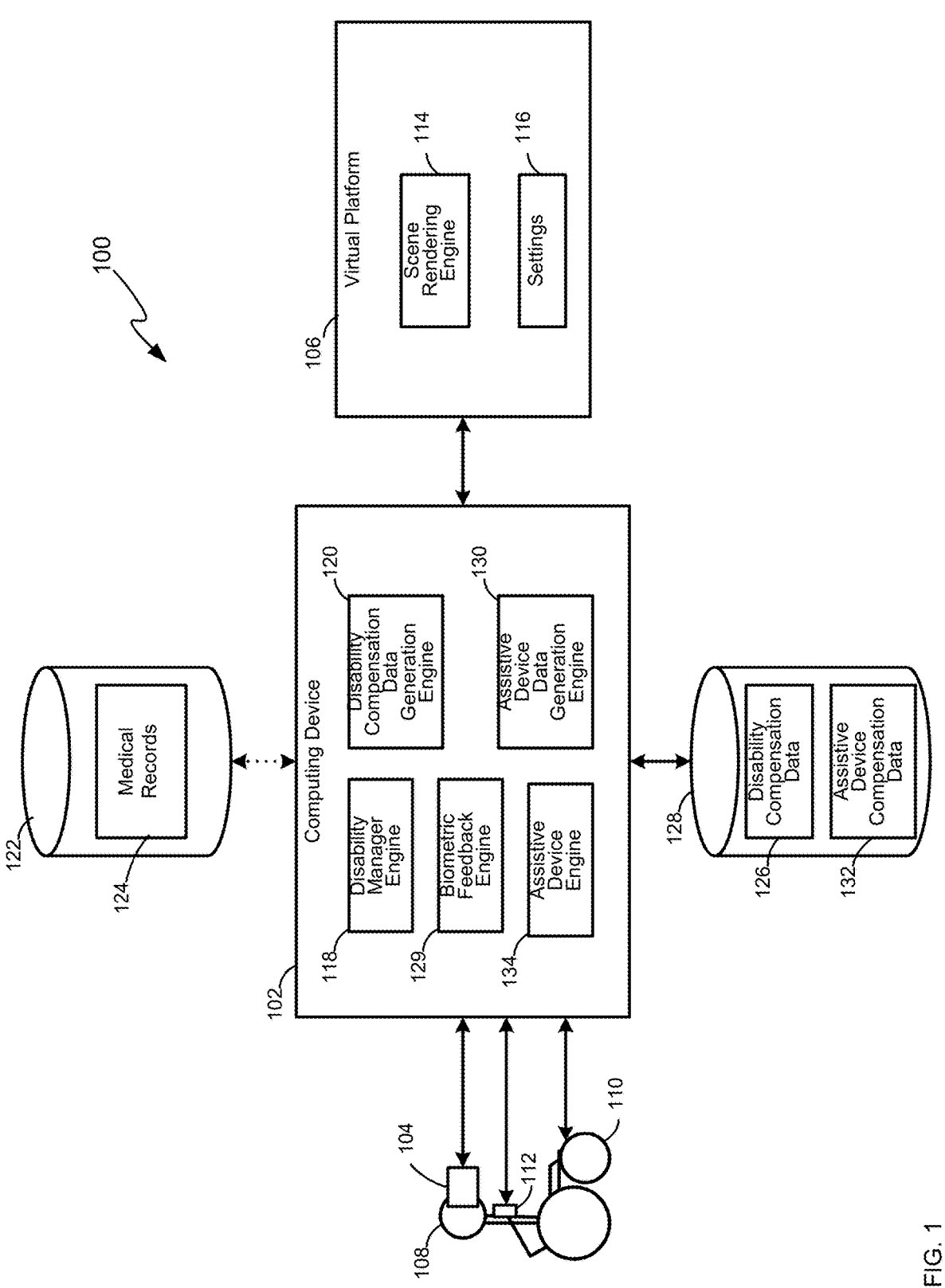
FIG. 1 depicts a system for secure access to virtual platforms, according to non-limiting examples.

FIG. 1 shows a system 100 for secure access to virtual platforms.

The system 100 will be described with respect to engines. As used herein, the term "engine" refers to hardware (e.g., a processor, such as a central processing unit (CPU), graphics processing unit (GPU), an integrated circuit or other circuitry) or a combination of hardware and software (e.g., programming such as machine- or processor-executable instructions, commands, or code such as firmware, a device driver, programming, object code, etc. as stored on hardware). Hardware includes a hardware element with no software elements such as an application specific integrated circuit (ASIC), a Field Programmable Gate Array (FPGA), a PAL (programmable array logic), a PLA (programmable logic array), a PLD (programmable logic device), etc. A combination of hardware and software includes software hosted at hardware (e.g., a software module that is stored at a processor-readable memory such as random access memory (RAM), a hard-disk or solid-state drive, resistive memory, or optical media such as a digital versatile disc (DVD), and/or implemented or interpreted by a processor), or hardware and software hosted at hardware.

Furthermore, the components of the system 100 are generally in communication via communication links, which are depicted in FIG. 1, and throughout the present specification, as double-ended arrows between respective components. The communication links include any suitable combination of wireless and/or wired communication networks and, similarly, the communication links may include any suitable combination of wireless and/or wired links.

As depicted, the system 100 comprises a computing device 102 in communication with a client device 104 and a virtual platform 106. For example, the computing device 102 may act as an intermediary between the client device 104 and the virtual platform 106, such that the client device 104 may access the virtual platform 106 via the client device 104, and/or the computing device 102 may control aspects of the virtual platform on behalf of the client device 104. While in examples as described herein (e.g., see FIG. 6) communication sessions between the client device 104 and the virtual platform 106 are depicted as occurring via a separate communication link therebetween (e.g., omitting the computing device 102), with the computing device 102 controlling aspects of the virtual platform 106 during the communication sessions, in other examples the communication session between the client device 104 and the virtual platform 106 may occur via the computing device 102.

While only one client device 104 is depicted, it understood that the system 100 may comprise a plurality of client devices that may engage in communication session with the virtual platform 106, and the computing device 102 may control respective aspects of the virtual platform on behalf of the plurality of client devices, including, but not limited to, the client device 104.

The client device 104 may comprise any suitable type of human-machine interface for interacting with the virtual platform 106. While as depicted the client device 104 comprises a headset, such as a virtual reality headset, and the like, the client device 104 may include, but is not limited to, a headset, a virtual reality suit, a flight simulator, a laptop computer, a desktop computer, a mobile phone, a tablet computer and any other device that may be used to receive content from the virtual platform 106 that complement the input and output hardware devices associated with the client device 104. It is contemplated that the client device 104 may include virtual or augmented reality gear complementary to virtual environments (e.g., virtual reality and/or augmented reality environments) that may be offered by the virtual platform 106, and/or any other suitable virtual platform. In particular, the client device 104 may comprise any suitable component, such as a display screen and a speaker, for providing rendered scenes of the virtual platform 106, as described herein.

The client device 104 is generally understood to be operated by a user 108 who may have a disability; for example, as depicted, the user 108 is interacting with an assistive device 110, as depicted, a wheelchair, which may assist the user 108 with their disability; for example, the user 108 may not be able to walk and may use the assistive device 110 for mobility.

However, it is understood that that the assistive device 110 may comprise any suitable assistive device, which may depend on a disability associated with the user 108. For example, the assistive device 110 may include, but is not limited to, a wheelchair, a scooter, a bed (e.g., such as a bed movable between different positions), a pressure sore prevention device (e.g., such as an alternating pressure sore mattress, and the like), a hearing aid, special glasses, amongst other possibilities, and/or combinations thereof.

However, it is understood that that the assistive device 110 is optional.

Furthermore, it is understood that a disability associated with the user 108 may not be visible. Rather, a disability associated with the user 108 may include, but is not limited to, inability to walk and/or stand, color blindness, vision loss, vision and/or light sensitivity, hearing loss, hearing and/or noise sensitivity, post-traumatic stress disorder (PTSD), depression, anxiety, amongst other possibilities, autism, phobias, and/or combinations thereof.

As depicted, the user 108 is wearing a biometric device 112, which may include, but is not limited to, a heart rate monitor, an oxygen level monitor, a blood pressure monitor, an eye monitor, and the like. In some examples, the biometric device 112 may be provided in a form of a smart watch configured to monitor heart rate, oxygen levels, and the like, of the user 108. In other examples, the biometric device 112 may be provided in a form of a chest strap, and/or a pressure cuff (e.g., interacting with an arm and/or a leg of the user 108), and the like, configured to monitor heart rate, oxygen levels, blood pressure, and the like, of the user 108. However, the biometric device 112 may be optional.

While the client device 104, the assistive device 110, and the biometric device 112 are depicted as being separate from each other, in some examples one or more of the client device 104, the assistive device 110, and the biometric device 112 may be combined. For example, the client device 104 may include a heartrate monitor and/or an eye monitor, and the like. Similarly, the client device 104 may include a hearing aid, and the like. Similarly, the biometric device 112 and the assistive device 110 may be combined; for example a wheelchair of the depicted assistive device 110 may comprise the biometric device 112 in a form of a blood pressure monitor that measures blood pressure in legs of the user 108.

As depicted, computing device 102 is optionally in communication with the assistive device 110 and the biometric device 112 via respective communication links. In such examples, it is understood that the assistive device 110 and the biometric device 112 are generally configured to communicate over such communication links, for example via respective communication interfaces.

However, while the client device 104, the assistive device 110, and the biometric device 112 are depicted as being in communication with the computing device 102 via separate communication links, in other examples, two or more of the client device 104, the assistive device 110, and the biometric device 112 may be in communication with the computing device 102 via one communication link. For example, two or more of the client device 104, the assistive device 110, and the biometric device 112 may be in local communication with each other (e.g., via respective communication interfaces), forming a personal area network, with one device, such as the client device 104, of the personal area network acting as a primary device via which communications with the computing device 102 occurs, for all devices of the personal area network, via a communication link between the primary device and the computing device 102.

The virtual platform 106 may be based on any present or future electronic media servers that publish and/or provide content for the client device 104 including, but not limited to, scene rendering data, representing rendered scenes. In particular, the virtual platform 106 may comprise an augmented reality and/or virtual reality platform, which may provide an augmented reality and/or virtual reality environment, such as a "metaverse" environment, and/or a virtual environment, and the like.

In particular, as depicted, the virtual platform 106 implements a scene rendering engine 114. The scene rendering engine 114 may render scenes, for example based on settings 116. Such scenes may include, but are not limited to, any suitable combination of visual scenes, aural scenes, haptic scenes, and the like (which may include, but are not limited to, visual data, aural data, vibration data, temperature data, olfactory data, and the like to be provided at a client device, such as the client device 104, during a communication session therebetween. Such scenes may be two-dimensional or three-dimensional, depending on capability of a client device for which the scenes are being rendered. In some examples, however, such scenes may be primarily and/or only aural using, for example descriptive video to explain non-depicted visual aspects of a scene (e.g., for visually impaired users). Furthermore, such scenes are understood to be compatible with the client device 104 (e.g. the client device 104 may or may not be configured to provide olfactory data which may hence be omitted from a scene that may otherwise include olfactory data). As the system 100 may comprise a plurality of client devices, the scene rendering engine 114 may render respective scenes for the plurality of client devices.

In general, access by the client device 104 to a virtual environment provided by the virtual platform 106 may occur by way of an avatar, and the like, which may be controlled by the user 108, via the client device 104, to navigate the virtual environment; the client device 104 may also be used to view and/or interact with content of the virtual environment.

The term avatar, as used herein, may refer to any two-dimensional and/or three-dimensional representation of the user 108 (or any other user) in the virtual environment, and which may be controlled via the client device 104 to interact with content of the virtual environment provided by the virtual platform 106. In instances where the virtual environment is primarily and/or only aural, such an avatar may still be two-dimensional and/or three-dimensional, as the avatar generally still moves through the virtual environment, and may be seen by other avatars of the virtual environment for whom the virtual environment may be rendered as two-dimensional and/or three-dimensional.

In particular, the scene rendering engine 114 may render scenes based on the settings 116, which may comprise respective settings for a plurality of client devices. Hence, while herein the settings 116 are described as being particular to the client device 104, it is understood that the settings 116 may include different settings for different client devices.

The scene rendering engine 114 may render scenes based on the settings 116 to control one or more of a viewing height of the scenes, a color scheme of the scenes, a brightness of the scenes, a volume of sound of the scenes, gravity in the scenes, accessibility in the scenes, a dimensionality of the scenes, a brightness of the scenes, a mode of a game of the scenes, amongst other possibilities, and/or combinations thereof. The settings 116 may additionally, or alternatively, include one or more of a difficulty level setting, a field of view setting, an audio mix setting, a language selection setting, a subtitle activation setting, a setting scene description mode setting, a text font setting, a font size setting, a contrast setting, a sound and/or graphical cues configuration setting, a key biding setting, a controller sensitivity setting, an avatar configuration setting, and the like. The settings 116 may comprise default values for such parameters.

For example, is understood that the user 108, via the client device 104, may control an avatar to engage with, and navigate the virtual environment, by way of the user 108 operating the client device 104 to provide commands to the virtual platform 106 with respect to orientation and/or movement, and the like, of the avatar in the virtual environment, and the scene rendering engine 114 may generate scene rendering data, corresponding to rendered scenes, accordingly, which are provided to the client device 104.

The client device 104 provides rendered scenes using such scene rendering data, using any suitable combination of hardware and/or output devices including, but not limited to a display screen, a speaker, and the like. Hereafter, the terms rendered scenes and scene rendering data may be used interchangeably for simplicity.

As previously mentioned, the user 108 may have a disability, and the scenes rendered by the scene rendering engine 114 may be adapted accordingly to accommodate a disability. For example, the color of the scenes may be adapted to account for color blindness of the user 108. Similarly, an avatar of the user 108 may be in a wheelchair, and a viewing height of the scenes may be adapted to be at an eye height of the avatar in a wheelchair (e.g., rather than at a standing height of the avatar). Similarly, an avatar of the user 108 may also be in a wheelchair, and accessibility of the scenes may be adapted such that curbs in the virtual environment are sloped and/or have ramps, buildings have ramps, and the like. Similarly, the user 108 may be hard of hearing and a volume of the scenes may be increased; conversely, in other examples, the user 108 may have PTSD (post-traumatic stress disorder) and a volume of the scenes may be decreased and/or loud noises in the scenes may be muted. Similarly, the user 108 may be depressed, and losing a game of the virtual environment provided by the virtual platform 106 may be problematic for the user 108; in these examples, the settings 116 may be adjusted such the game is played in a so-called "god" mode, where the user 108 cannot lose the game, and the like.

Hence, in general, the settings 116 may be adjusted to adapt the scenes for the disability associated with the user 108, and the scene rendering engine 114 may use such adjusted settings 116 to render scenes, which are provided to the client device 104. It is further understood that the settings 116 may be adjusted from default settings, which may include, but are not limited to, a default viewing height corresponding to a standing height of an avatar, a default color scheme, a default volume, and the like.

However, a significant security issue exists in such a scenario. For example, when the virtual platform 106 is provided, an entity that operates the virtual platform 106 may have access to information that includes a disability associated with the user 108 in order to adapt the virtual environment to the disability. Such information may be vulnerable to leaks and/or hacking at virtual platform 106, for example by bad actors. Alternatively, and/or in addition, the user 108 may inadvertently provide permission to the entity to provide their information, that includes a disability associated with the user 108, to third parties, and at least the information that includes a disability associated with the user 108 may be used against the user 108 by such third parties.

Hence, to minimize a risk of such information being leaked and/or to provide secure access to the virtual platform 106, as depicted, the computing device 102 comprises a disability manager engine 118, generally configured to adjust the settings 116 of the virtual platform 106 to compensate for a disability associated with the user 108 of the client device 104, without providing information related to the disability associated with the user 108, and/or personal identifiable information of the user 108, to the virtual platform 106, as described herein. Furthermore, as depicted, the computing device 102 comprises a disability compensation data generation engine 120 generally configured to generate disability compensation data used by the disability manager engine 118 to adjust the settings 116.

For example, as depicted, the computing device 102 may be provided with temporary access to a memory 122, for example as depicted in the form of a database, which stores medical records 124 associated with the user 108. The medical records 124 may contain specific information related to a disability associated with the user 108, including, but not limited to, medical diagnoses, prescriptions (e.g., for drugs and/or assistive devices), information defining the assistive device 110, medical imaging data (e.g., X-Rays and/or magnetic resonance images), amongst other possibilities. Such medical records 124 may hence generally include personal identifiable information (PII), which, if provided to the virtual platform 106 might enable to the scene rendering engine 114 to better render scenes, but which would also be a significant security risk to the user 108. The memory 122 may be operated by a medical entity, and/or any other suitable entity.

As will be described herein, the computing device 102 may be provided with at least temporary access to the memory 122 (e.g., such temporary access indicated by a dashed double ended arrow therebetween, indicating a communication link therebetween may be temporary), such that the computing device 102 may access the medical records 124, for example to retrieve a copy of the medical records 124. Such access may be granted by the user 108, for example via the user 108 operating the client device 104, or another client device, to provide a network address of the memory 122 to the computing device 102 and/or otherwise grant permission of the computing device 102 to the memory 122 in any suitable manner. Such access may occur in a secure manner, for example, by way of use of any suitable combination of passwords, encryption, virtual private networks, and the like, amongst other possibilities.

However, the medical records 124 may be provided to the computing device 102 in any suitable manner. For example, the medical records 124 may be provided to the computing device 102 from a medical entity, upon being given permission by the user 108, and/or the user 108 (or another user with access to the medical records 124) may obtain the medical records 124 and provide the medical records 124 to the computing device 102 via the client device 104, and/or any other suitable client device, and the like.

The medical records 124 may be input to the disability compensation data generation engine 120, which may output disability compensation data 126. The disability compensation data 126 is generally indicative of how to compensate for a disability associated with the user 108 of the client device 104 within virtual platforms, including, but not limited to, the virtual platform 106. Furthermore, the disability compensation data generation engine 120 further anonymizes the disability compensation data 126 to remove personal identifiable information associated with the user 108, including, but not limited to, information defining the disability associated with the user 108.

For example, the disability compensation data generation engine 120 may comprise one or more machine learning algorithms, and the like, trained to convert medical records (e.g., that may include, but are not limited to, medical diagnoses, prescriptions, information defining the assistive device 110, medical imaging data, amongst other possibilities) to disability compensation data, and to remove PII from medical records. However, alternatively, or in addition, the disability compensation data generation engine 120 may provide such functionality via any suitable programmatic algorithm.

For example, when the medical records 124 indicate that the user 108 uses a wheelchair (e.g., the assistive device 110), the disability compensation data generation engine 120 may determine a viewing height for rendered scenes of a virtual platform that is compatible for a user in a wheelchair, for example when an avatar thereof is also in a wheelchair. Such a viewing height may be stored in the disability compensation data 126 without reference to the user 108 using a wheelchair, and/or why the user 108 uses a wheelchair, and/or associated treatments, and the like. Put another way, any reference to a medical diagnosis, prescription for drugs, a prescription for an assistive device, and/or any other PII from the medical records 124 that lead to the determination of the viewing height is omitted from the disability compensation data 126. The viewing height stored at the disability compensation data 126 may in any suitable format, such as meters and/or centimeters, feet and inches, amongst other possibilities.

Similarly, when the medical records 124 indicate that the user 108 is color blind, the disability compensation data generation engine 120 may determine a color scheme for rendered scenes of a virtual platform that is compatible with a user who is color blind. Such a color scheme may be stored in the disability compensation data 126 without reference to the user 108 being color blind, and/or why the user 108 is color blind, and/or associated treatments, and the like. Put another way, any reference to a medical diagnosis, prescription for drugs, a prescription for an assistive device for color blindness (e.g., any special glasses), and/or any other PII from the medical records 124 that lead to the determination of the color scheme is omitted from the disability compensation data 126. The color scheme stored at the disability compensation data 126 may in any suitable format, such as RGB (red-green-blue) coordinates, a color temperature, amongst other possibilities.

Similarly, when the medical records 124 indicate that the user 108 has PTSD and/or is hard of hearing, and the like, the disability compensation data generation engine 120 may determine a volume for sounds for rendered scenes of a virtual platform that is compatible for a user who has PTSD and/or is hard of hearing, and the like, and a mix of sounds for rendered scenes of a virtual platform that is compatible for a user who has PTSD and/or is hard of hearing, and the like (e.g. to control frequencies of such sounds, and the like, for example to reduce low frequency sounds and/or high frequency sounds to which a user who has PTSD, and the like, may be sensitive). Such a volume may be stored in the disability compensation data 126 without reference to the user 108 having PTSD and/or being hard of hearing, and/or why the user 108 has PTSD and/or is hard of hearing, and/or associated treatments, and the like. Put another way, any reference to a medical diagnosis, prescription for drugs, a prescription for an assistive device for treating PTSD and/or being hard of hearing (e.g., any hearing aids), and/or any other PII from the medical records 124 that lead to the determination of the volume is omitted from the disability compensation data 126. The volume stored at the disability compensation data 126 may in any suitable format, such as on a scale of 1 to 100 (e.g., with 1 and 100 respectively being a lowest and highest possible volume of a scene rendered by a virtual platform), decibels, amongst other possibilities.

It is further understood that any copies of the medical records 124 at the computing device 102 are deleted, for example once the medical records 124 are processed by the disability compensation data generation engine 120 and/or once the disability compensation data 126 is stored at the memory 128.

It is further understood that the disability compensation data 126 may or may not be stored in a format that is compatible with, and/or the same as, the settings 116, though the disability compensation data 126 generally represents how the settings 116 are to be adjusted to control the virtual platform 106, and in particular the scene rendering engine 114, to compensate for a disability associated with the user 108 of the client device 104 within the virtual platform 106 and/or a virtual environment thereof.

However in some examples, the disability compensation data 126 may comprise specific indications for adjusting the settings 116 of the virtual platform 106 to compensate for a disability associated with the user 108, the specific indications including specific settings adjustments particular to the virtual platform 106, as described herein. Put another way, in some examples, the disability compensation data 126 may be in a same format as the settings 116.

However, in other examples, the disability compensation data 126 may comprise generic indications for adjusting the settings 116 of the virtual platform 106 to compensate for a disability associated with the user 108, the generic indications omitting specific settings adjustments of the virtual platform 106. Put another way, in some examples, the disability compensation data 126 may be in a different format from the settings 116.

The disability manager engine 118 may receive, as input, disability compensation data 126 and adjust the settings 116 of the virtual platform 106 accordingly, for example when the client device 104 communicates with the computing device 102 (e.g., under operation by the user 108), to begin a communication session with the virtual platform 106. It is hence understood that generation of the disability compensation data 126 may occur prior to such a communication session.

Furthermore, as the disability compensation data 126 may not be in a format compatible with the settings 116, the disability manager engine 118 may translate the disability compensation data 126 into a format compatible with the settings 116. In particular, while only one virtual platform 106 is depicted, the system 100 may comprise a plurality of virtual platforms having respective scene rendering engines and respective settings, and the client device 104 may initiate communication sessions with any of such a plurality of virtual platforms via the computing device 102; the disability manager engine 118 may hence be configured to adjust respective settings of any suitable virtual platform using the disability compensation data 126. Put another way, the disability manager engine 118 may translate the disability compensation data 126 into a format compatible with settings of one or more virtual platforms, including, but not limited to, the settings 116 of the virtual platform 106.

In this manner, the settings 116 of the virtual platform 106 may be adjusted for the user 108, without providing any PII associated with the user 108 to the virtual platform 106 (e.g., or any virtual platform). Furthermore, as any copies of the medical records 124 are deleted from the computing device 102, neither does the computing device 102 store any PII associated with the user 108. As such, the client device 104 may more securely access the virtual platform 106, while both having the settings 116 adjusted to compensate for a disability and without exposing PII of the user 108 to the virtual platform 106 and/or without storing PII of the user 108 at the virtual platform 106. Similarly, the PII is not stored at the computing device 102 and, after any copies of the medical records 124 are deleted, neither does the computing device 102 have access to the PII of the user 108.

It is furthermore, understood that while the memory 128 is depicted as separate from the computing device 102, the memory 128 may be a component of the computing device 102.

Alternatively, the memory 128 may be a component of the client device 104, such that the client device 104 stores the disability compensation data 126 (e.g., in an account profile), and provides the disability compensation data 126 to the computing device 102 when initiating a communication session with the virtual platform 106 via the computing device 102. In some of these examples, the client device 104 may implement the disability compensation data generation engine 120 and generate, and store, the disability compensation data 126.

In some examples, the disability compensation data 126 may be stored, at the memory 128, in association with an identifier of the client device 104 and/or the user 108. In these examples, when the client device 104 (and/or the user 108 using any suitable client device, which may be different from the client device 104), initiates a communication session with the virtual platform 106 (or any other suitable virtual platform), via the computing device 102, the client device 104 (or another client device used by the user 108), may provide such an identifier to the computing device 102, which may retrieve the disability compensation data 126 from the memory 128, accordingly, and use the disability compensation data 126, as retrieved, to adjust the settings 116 of the virtual platform 106 (or any other suitable virtual platform), accordingly.

Indeed, the memory 128 may store a plurality of sets of respective disability compensation data for a plurality of users (e.g., and/or a plurality of client devices), and when a given user initiates a communication session with virtual platform via the computing device 102, using a respective client device, the computing device 102 may retrieve the respective disability compensation data accordingly based, for example, on a respective identifier provided by the respective client device. Such an identifier may include, but is not limited to, a user name of a user for logging into the computing device 102 (and/or a virtual platform). Indeed, the computing device 102 and/or the disability manager engine 118 may be configured to control respective settings, including the settings 116, across a plurality of virtual platforms, including the virtual platform 106, and such control may depend on respective parameters of the respective settings. Hence, the computing device 102 and/or the disability manager engine 118 may further simplify control of settings across a plurality of virtual platforms.

It is further understood that, during a communication session between the client device 104 and the virtual platform 106, the biometric device 112 may provide biometric data to the computing device 102, which may adjust the settings 116 of the virtual platform 106, accordingly, based on the biometric data, using, for example, a biometric feedback engine 129 trained to perform such functionality. In particular, the biometric feedback engine 129 may receive the biometric data and output adjusted settings, which may be used to accordingly adjust the settings 116 of the virtual platform 106. An example of such an adjustment is described with respect to FIG. 8. The biometric data and/or output adjusted settings, which may also be used to adjust the disability compensation data 126.

For example, when the biometric data from the biometric device 112 indicates that a heartrate of the user 108 has exceeded a threshold heartrate (e.g., such as 80 beats per minute (BPM), 90 BPM, 100 BPM, amongst other possibilities), the computing device 102 and/or the biometric feedback engine 129 may adjust a volume (e.g., a scene volume) of the settings 116 to a lower volume (e.g., relative to a current volume), and/or adjust a brightness (e.g., a scene brightness) of the settings 116 to a lower brightness (e.g., relative to a current brightness), and the like. The computing device 102 and/or the biometric feedback engine 129 may continue to adjust the settings 116 accordingly in a feedback loop as biometric data from the biometric device 112 continues to be received.

Furthermore, when a communication session ends, and/or at any other suitable time, the computing device 102 may adjust the disability compensation data 126 to store any updates to the settings 116 that were based on biometric data from the biometric device 112, for example an adjusted volume, and adjusted brightness, and the like, translated into format of the disability compensation data 126. Furthermore, any biometric data may be deleted from a memory of the computing device 102, as such biometric data may be at least temporarily stored in cache, and the like, of the computing device 102. Put another way, the computing device 102 may not store the biometric data, which may represent PII of the user 108.

Similarly, during a communication session between the client device 104 and the virtual platform 106, the computing device 102 may cause and/or control the assistive device 110 to adjust, to one or more of alleviate and avoid one or more disabilities of the user 108. However, such control may also occur without storing of PII.

It is further understood that, during a communication session between the client device 104 and the virtual platform 106, the assistive device 110 may be adjusted to one or more of alleviate and avoid one or more disabilities of the user 108 of the client device 104. An example of such an adjustment is described with respect to FIG. 9.

For example, as depicted, the computing device 102 may further comprise an assistive device data generation engine 130 configured to receive the medical records 124 as input, and output assistive device compensation data 132 for respective assistive devices associated with the user 108, such as the assistive device 110. Such assistive device compensation data 132 may be used to cause and/or control an assistive device to adjust, to one or more of alleviate and avoid one or more disabilities of a user.

For example, when the medical records 124 indicate that the user 108 uses the assistive device 110 in the form of a bed and/or wheelchair movable between different positions, and/or which includes a pressure sore prevention device, the assistive device data generation engine 130 may generate settings for controlling such a bed and/or wheelchair, but without storing information indicating that the settings are for such a bed and/or wheelchair. Such settings may be stored in the assistive device compensation data 132, or another set of data. In particular, such settings may control the bed and/or wheelchair to move between different positions periodically and/or adjust the pressure sore prevention device periodically, to prevent pressure sores and/or bedsores, and the like.

In some examples, such adjustments may be based on biometric data from the biometric device 112.

For example, when the biometric data from the biometric device 112 indicates that a blood pressure of the user 108 has exceeded a threshold blood pressure (e.g., such as 130 mm Hg systolic, 135 mm Hg systolic, amongst other possibilities), the computing device 102 may adjust the assistive device 110, in the form of a wheelchair or bed, to reposition the user 108 from a primarily prone position to a relatively elevated position, which may lower blood pressure and/or prevent bedsores. The assistive device compensation data 132 may indicate how to adjust the assistive device 110 when such threshold are met and/or exceeded (and/or, in some when certain biometric data falls below a respective threshold, such as a low blood pressure threshold, and the like).

Having described an overview of system 100, hardware infrastructure of certain components of the system 100 will next be described.

Figure 2:
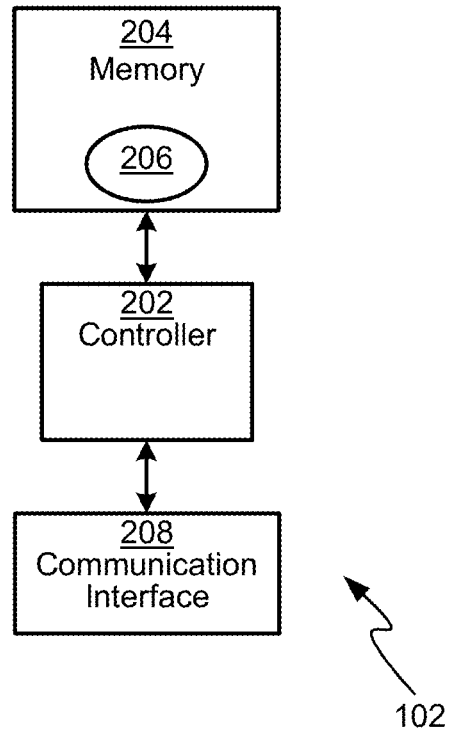
FIG. 2 depicts a block diagram of a device for secure access to virtual platforms, according to non-limiting examples.

Attention is next directed to FIG. 2, which depicts details of the computing device 102. The computing device 102 may comprise one or more computing devices, and/or one or more servers and/or one or more cloud computing devices, and the like. Alternatively, and/or in addition, the computing device 102 may comprise one or more personal computers and/or one or more laptops, and/or any other suitable computing device. In some examples, the computing device 102 may be a component of a game launcher system; in these examples, a virtual platform of the virtual platform 106 may comprise a game. In some examples, the computing device 102 may be combined with the client device 104.

In the depicted example of FIG. 2, the computing device 102 includes at least one controller 202 interconnected with a memory 204, storing one or more applications 206, and a communication interface 208.

The controller 202 may be implemented as a plurality of processors or one or more multi-core processors and/or may include one or more central processing units (CPUs). However, the controller 202 may comprise any suitable combination of processors, ASICs, FPGAS, PALs, PLAS, PLDs, and the like. The controller 202 be configured to execute different programing instructions, as described herein.

The memory 204 may include any suitable combination of non-volatile and volatile memories. A non-volatile memory, of the memory 204, may be based on any persistent memory technology, such as an Erasable Electronic Programmable Read Only Memory ("EEPROM"), flash memory, solid-state hard disk (SSD), other type of hard-disk, or combinations of them. Hence, a non-volatile memory, of the memory 204, may also be described as a non-transitory computer readable media.

A volatile memory, of the memory 204, may be based on any random access memory (RAM) technology. For example, volatile memory, of the memory 204, may be based on a Double Data Rate (DDR) Synchronous Dynamic Random-Access Memory (SDRAM).

Other types of non-volatile and/or volatile memory are contemplated and/or may be provided.

The controller 202 and the memory 204 may be generally comprised of one or more integrated circuits (ICs).

The controller 202 is also interconnected with the communication interface 208, which enables the computing device 102 to communicate with the other components of the system 100, for example via any suitable network. The communication interface 208 therefore may include any suitable components (e.g., network interface controllers (NICs), radio units, and the like) to communicate via any suitable network. The specific components of the communication interface 208 may be selected based upon the nature of a network used to communicate, and/or local communication between components of the system 100, and the like.

While not depicted in FIG. 2, the computing device 102 may also include input and output devices connected to the controller 202, such as keyboards, mice, display screens, and the like (not shown).

The components of the computing device 102 may be deployed in a single enclosure, or in a distributed format. In some examples, therefore, the computing device 102 may include a plurality of controllers and/or processors, either sharing the memory 204 and the communication interface 208, or having distinct associated memories and communication interfaces. As such, it is understood that the memory 204 and/or a portion of the memory 204 may be internal (e.g., as depicted) or external to the computing device 102; regardless, the controller 202 is understood to have access to the memory 204. In some examples, the memory 204 may comprise the memory 128 and/or a portion of the memory 128, and hence the memory 204 may store one or more of the disability compensation data 126 and the assistive device compensation data 132.

The memory 204 also stores computer-readable programming instructions, executable by the controller 202, in the form of various applications, including the application 206. As will be understood by those skilled in the art, the controller 202 executes the instructions of the application 206 (and any other suitable applications) in order to perform various actions defined by the instructions contained therein including, but not limited to, the blocks of a method described with respect to FIG. 3. In the description below, the controller 202, and more generally the computing device 102, are understood to be configured to perform those actions. It will be understood that they are so configured via the execution (by the controller 202) of the instructions of the applications stored in memory 204.

Furthermore, the application 206 may include any suitable modules and/or components for implementing the engines 118, 120, 129, 130, 134. Furthermore, such modules and/or components may comprise any suitable combination of programmatic algorithms and/or machine learning algorithms. However, functionality of any of the engines 118, 120, 129, 130, 134 may be combined in any suitable manner, and in some examples, one or more of the engines 118, 120, 129, 130, 134 may be omitted; rather, functionality of any omitted engines 118, 120, 129, 130, 134 may be implemented by the application 206.

When such modules and/or components include machine learning algorithms, it is understood that the machine learning algorithms may be operated in a training mode to train the machine learning algorithms to perform functionality as described herein. In particular, the machine learning algorithms may be operated according to a machine learning training feedback loop in which previous input and previous output are used as training data labelled with a score, and the like, indicating accuracy and/or adequacy, and the like of the previous output. Such a score may be generated by the client device 104, and provided to the computing device 102, and may represent a score assigned to the output by the user 108. For example, the user 108 may score the disability compensation data 126 used to control the settings 116 of the virtual platform, and such a score may be used to train a machine learning algorithm of the disability compensation data generation engine 120 to better output disability compensation data from medical records; it is understood, however, in these examples, that the computing device 102 may again retrieve a copy of the medical records 124 for such training, which may again be deleted after such training, and the like. The assistive device data generation engine 130 may be similarly trained.

Indeed, after such training, the medical records 124 may again be used to generate updated disability compensation data 126 and/or assistive device compensation data 132 via a better trained disability compensation data generation engine 120 and/or a better trained assistive device data generation engine 130. Such generation may occur after the medical records 124 are again retrieved for the training and before any copies of the medical records 124 are again deleted, or such generation may occur by way of yet again retrieving a copy of the medical records 124, which are again retrieved are again deleted after generation of the updated disability compensation data 126 and/or assistive device compensation data 132.

The infrastructure of the computing device 102, or a variant thereon, can be used to implement any of the computing components of the system 100, including, but not limited to, the client device 104 and/or the virtual platform 106. Furthermore, the computing device 102 and/or the virtual platform 106 may also be implemented as virtual machines and/or with mirror images to provide load balancing. Functions of the computing device 102 may also be distributed amongst the client device 104 and/or the virtual platform 106, thereby obviating the need for an intermediation computing device 102. Similarly, a plurality of computing devices 102 may be provided.

Furthermore, it is understood that the core components of the controller 202, the memory 204, and the communication interface 208, as described in relation to the computing device 102, have analogues in the different form factors of client machines such as those that can be used to implement the client device 104. The client device 104 may be based on computer workstations, laptop computers, tablet computers, mobile telephony devices or the like, and may include any suitable augmented reality and/or virtual reality human-machine interfaces (HMIs) and/or hardware interfaces including, but not limited to, any suitable combination of input devices and output devices (e.g., such as keyboards, pointing devices, touch devices, display screens, haptic devices, and the like).

Attention is now directed to FIG. 3, which depicts a flowchart representative of a method 300 for secure access to virtual platforms, such as the virtual platform 106. The operations of the method 300 of FIG. 3 correspond to machine readable instructions that are executed by the computing device 102, and specifically the controller 202. In the illustrated example, the instructions represented by the blocks of FIG. 3 are stored at the memory 204 for example, as the application 206. The method 300 of FIG. 3 is one way in which the controller 202 and/or the computing device 102 and/or the system 100 may be configured. Furthermore, the following discussion of the method 300 of FIG. 3 will lead to a further understanding of the system 100, and its various components.

Put another way, the computing device 102 may comprise the controller 202 and the memory 204 storing instructions executable on the controller 202, to cause the controller 202 to implement the blocks of the method 300.

The method 300 of FIG. 3 need not be performed in the exact sequence as shown, or with certain blocks omitted, performed in parallel or in a different order than shown. Accordingly, the elements of method 300 are referred to herein as "blocks" rather than "steps." The method 300 of FIG. 3 may be implemented on variations of the system 100, as well.

At a block 302, the controller 202 and/or the computing device 102, establishes a communication session between a client device 104 and a virtual platform 106, the client device 104 configured to provide rendered scenes of the virtual platform 106 based on scene rendering data generated by the virtual platform 106. The scene rendering data may comprise rendered scenes and/or commands for rendering such scenes at the client device 104. An example of such a communication is described below with respect to FIG. 6.

At a block 304, the controller 202 and/or the computing device 102, accesses, at a memory 128, disability compensation data 126 indicative of how to compensate for a disability associated with a user 108 of the client device 104 within virtual platforms, the disability compensation data 126 anonymized to remove personal identifiable information associated with the user 108. An example of such access is also described below with respect to FIG. 6.

At a block 306, the controller 202 and/or the computing device 102, adjusts settings 116 of the virtual platform 106 according to the disability compensation data 126 to control the virtual platform 106 to generate the scene rendering data according to the settings 116 as adjusted, such that the client device 104 renders scenes of the virtual platform 106 according to the scene rendering data during the communication session to replicate the disability for an avatar associated with the user 108 in the virtual platform 106. An example of such adjustment is also described below with respect to FIG. 6.

The method 300 may include further aspects.

For example, the method 300 may further comprise the controller 202 and/or the computing device 102 accessing the medical records 124 associated with the user 108; generating the disability compensation data 126 from the medical records 124 including removing any of the personal identifiable information in the medical records 124 from the disability compensation data 126; and deleting copies of the medical records 124 generated when accessing the medical records 124 and generating the disability compensation data

126. Hence, the disability compensation data 126 is understood to omit PII associated with the user 108 and, more specifically, the disability compensation data 126 omits any reference to a type of the disability associated with the user 108. An example of such generation is described below with respect to FIG. 4.

In some examples, the disability compensation data 126 may comprise: specific indications for adjusting the settings 116 of the virtual platform 106 to compensate for the disability associated with the user 108, the specific indications including specific settings adjustments. For example, the specific indications for adjusting the settings 116 of the virtual platform 106 may be in a same format as the settings 116.

However, in other examples, the disability compensation data 126 may comprise: generic indications for adjusting the settings 116 of the virtual platform 106 to compensate for the disability associated with the user 108, the generic indications omitting specific settings adjustments. For example the generic indications for adjusting the settings 116 of the virtual platform 106 may be in a different format as the settings 116. In these examples, adjusting (e.g., at the block 306) the settings 116 of the virtual platform 106 according to the disability compensation data 126 may comprise: translating the generic indications for adjusting the settings 116 into specific setting adjustments to the settings 116. Hence, in these examples, the generic indications of the disability compensation data 126 may be used for any suitable virtual platform with the controller 202 and/or the computing device 102 translating the generic indications for adjusting settings of any suitable virtual platform into specific setting adjustments to the settings of any suitable virtual platform. Put another way, the controller 202 and/or the computing device 102 may translate the generic indications of the disability compensation data 126 into a format compatible with settings of any suitable virtual platform.

In some examples, the method 300 may further comprise the controller 202 and/or the computing device 102: receiving biometric data associated with the user 108 during the communication session; and further adjusting the settings 116 of the virtual platform 106 based on the biometric data. An example of such adjustment is described below with respect to FIG. 8.

Similarly, in some examples, the method 300 may further comprise the controller 202 and/or the computing device 102: receiving biometric data associated with the user 108 during the communication session; and adjusting the disability compensation data 126 based on the biometric data. Such examples have been previously described.

In some examples, the method 300 may further comprise the controller 202 and/or the computing device 102: causing an assistive device 110, used by the user 108 of the client device 104, to adjust, to one or more of alleviate and avoid one or more disabilities of the user 108 of the client device 104. An example of such adjustment is described below with respect to FIG. 9.

In some examples, the method 300 may further comprise the controller 202 and/or the computing device 102: receiving, from the client device 104, an indication to adjust the settings 116 of the virtual platform 106; and adjusting the settings 116 based on the indication, wherein the indication comprises one of: a first indication to replicate, or compensate for, the disability (e.g., of the user 108) for the avatar associated with the user in the virtual platform 106; a second indication to partially replicate, or partially compensate for, the disability for the avatar in the virtual platform 106; a third indication to stop replicating, or not compensate for, the disability for the avatar in the virtual platform 106; and a fourth indication to simulate, or compensate for, a given disability for the avatar in the virtual platform 106.

Indeed, each of the first, second, third, and fourth indications may cause the virtual environment provided by the virtual platform 106 to the client device 104 to be placed into a different mode for the client device 104.

For example, at the client device 104, the user 108 may be provided with an interface, such as a graphical user interface (GUI), for selecting a mode for the virtual environment provided by the virtual platform 106 to the client device 104. The user 108 may select a mode using any suitable input device of the client device 104. An example of such a GUI is described below with respect to FIG. 5.

Such modes may include, but are not limited to:

A first mode corresponding to the first indication. In the first mode, the settings 116 are adjusted such that the scene rendering engine 114 replicates, in rendered scenes generated by the scene rendering engine 114, the disability for the avatar associated with the user 108 in the virtual platform 106, for example based on the disability compensation data 126. Hence, in the first mode, the settings 116 are adjusted according to the method 300.

A second mode corresponding to the second indication. In the second mode, the settings 116 are adjusted such that the scene rendering engine 114 partially replicates, or partially compensates for, in rendered scenes generated by the scene rendering engine 114, the disability for the avatar associated with the user 108 in the virtual platform 106, for example based on the disability compensation data 126. For example, in the interface provided by the client device 104, the user 108 may select, which portions of a disability to replicate and/or which portions of a disability not to replicate. In a particular example, when the user 108 is unable to walk and/or stand and experiences hearing loss, the user 108 may choose to not replicate their being unable to walk and/or stand, but the user 108 may choose to replicate the hearing loss such that the settings 116 are adjusted to raise a volume of rendered scenes. Hence, in these examples, the user 108 may turn on and turn off replication of any disability, and/or compensation thereof, in the virtual environment of the virtual platform 106. Hence, in the second mode, the settings 116 are partially adjusted according to the method 300.

A third mode corresponding to the third indication. In the third mode, the settings 116 are not adjusted from default settings, such that the scene rendering engine 114 stops replicating and/or does not replicate, in rendered scenes generated by the scene rendering engine 114, the disability for the avatar associated with the user 108 in the virtual platform 106. Hence, in these examples, the disability compensation data 126 is not used to adjust the settings 116, but rather default settings 116 may be used by the scene rendering engine 114 to render scenes. Hence, in the third mode, the settings 116 may not be adjusted according to the method 300.

A fourth mode corresponding to the fourth indication. In the fourth mode, the settings 116 are adjusted such that the scene rendering engine 114 simulates, and/or compensates for, a given disability, in rendered scenes generated by the scene rendering engine 114. For example, the user 108, or another user of the client device 104, may choose, using the interface, to simulate and/or compensate for a disability they may not have. In a specific example, the user 108, using the interface, may choose to simulate and/or compensate for PTSD when they may not have PTSD, for example to cause rendered scenes generated by the scene rendering engine 114 to be provided at a lower volume and/or a lower brightness, as compared to default settings 116. Hence, in the fourth mode, the settings 116 are adjusted, but according to a selected disability, and not necessarily a disability associated with the user 108. The adjustment of the settings may otherwise occur according to the method 300.

Attention is next directed to FIG. 4, FIG. 5, FIG. 6, FIG. 7, FIG. 8 and FIG. 9, which depicts an example of aspects of the method 300. FIG. 4, FIG. 6, FIG. 8 and FIG. 9 are substantially similar to FIG. 1, with like components having like numbers. While for simplicity not all components of FIG. 1 are depicted in FIG. 4, FIG. 6, FIG. 8 and FIG. 9, such components are nonetheless understood to be present, unless otherwise described.

Figure 4:
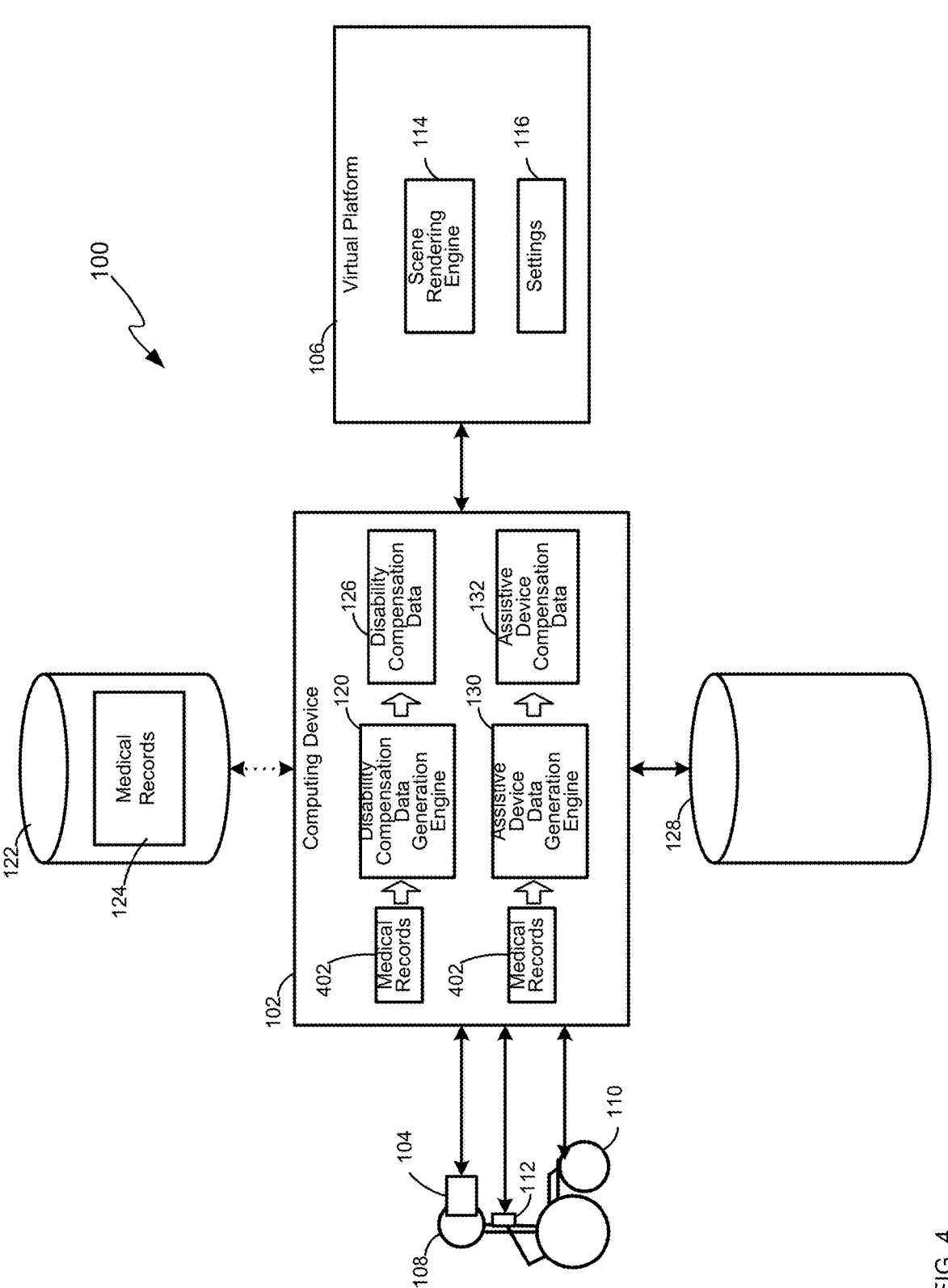
FIG. 4 depicts the system of FIG. 1 implementing aspects of a method for secure access to virtual platforms, according to non-limiting examples.

Attention is next directed to FIG. 4, which depicts generation of the disability compensation data 126 according to one example, and the optional generation of the assistive device compensation data 132. As depicted, a copy 402 of the medical records 124 has been retrieved from the memory 122 by the computing device 102, and the copy 402 of the medical records 124 is input to the disability compensation data generation engine 120, which outputs the disability compensation data 126, with any PII of the medical records 124 omitted from the disability compensation data 126.

For example, the medical records 124 may indicate the user 108 is in a wheelchair and has hearing loss, and the disability compensation data generation engine 120 may output a viewing height of 168 cm (amongst other possibilities), and a volume of 90% (amongst other possibilities), which may be stored at the disability compensation data 126.

Similarly, the copy 402 of the medical records 124 is input to the assistive device data generation engine 130, which outputs the assistive device compensation data 132, with any PII of the medical records 124 omitted from the assistive device compensation data 132.

For example, the medical records 124 may indicate the user 108 is in a wheelchair that has a pressure sore prevention device, and the assistive device data generation engine 130 may output a periodicity (e.g., such as every 5 minutes, amongst other possibilities, and which may depend on other medical information of the user 108 in the medical records 124) to alternate cells of the pressure sore prevention device, while the user 108 is logged into the virtual platform 106, which may be stored at the disability compensation data 126.

It is understood that the copy 402 of the medical records 124 is deleted from the computing device 102, and the disability compensation data 126 and the assistive device compensation data 132 is stored at the memory 128.

Attention is next directed to FIG. 5, which depicts a GUI 502 provided at the client device 104, the GUI 502 providing selectable options (e.g., labelled, "1", "2", "3" and "4") for selecting a mode of the virtual environment of the virtual platform 106. For example, the GUI 502 may be provided when the client device 104 logs into the computing device 102, for example to initiate a communication session with the virtual platform 106.

Selectable option "1" may be for replicating and/or compensating for a disability associated with the user 108 for an avatar associated with the user 108 in the virtual platform 106. When option "1" is selected, the client device 104 may return an indication of selected option "1" to the computing device 102, which then inputs the disability compensation data 126 to the disability manager engine 118 accordingly, as described with respect to FIG. 6.

Selectable option "2" may be for partially replicating and/or compensating for, a disability associated with the user 108 for an avatar associated with the user 108 in the virtual platform 106. For example, option "2" is provided with further selectable options 504 for selecting which disabilities of the user 108 may be replicated and/or compensated for, such as being "Unable To Walk" and "Hearing Loss". It is understood that in these examples, the options 504 may be provided in a manner that preserves the PII of the user 108, for example as such options 504 may reveal disabilities of the user 108.

For example, the options 504 may be stored as encrypted data at the memory 128, for example encrypted with a cryptographic key, and the computing device 102 may not have access to a complementary key for decrypting the encrypted data of the options 504. However, the client device 104 may have such a complementary key. The encrypted data of the options 504 may be provided to the client device 104 by the computing device 102 as a component of the GUI 502, and the client device 104 may decrypt the options 504 and be used to select one or more of the decrypted options 504 accordingly. Furthermore, the decrypted options 504 may be respectively mapped to given data of the disability compensation data 126. Hence, when one or more of the decrypted options 504 are selected (e.g., presuming option "2" is selected), the client device 104 may return an indication of a selected option 504 to the computing device 102, and/or an indication of the given data of the disability compensation data 126 to which the selected option 504 is mapped, but without indicating which disability a selected option 504 relates to. The computing device 102 may receive such an indication, and select a portion of the disability compensation data 126 that corresponds to the selected option 504. The computing device 102 may input such a portion of the disability compensation data 126 to the disability manager engine 118 accordingly, and adjust the settings 116 accordingly. Furthermore, option "2" may not be provided when only one option is available; in this instance option "2" and option "3", as next described, may be similar and/or combined (e.g., as partial replication may not be possible when the user 108 has only disability).

Selectable option "3" may be for not replicating and/or not compensating for a disability associated with the user 108 for an avatar associated with the user 108 in the virtual platform 106. When option "3" is selected, the client device 104 may return an indication of selected option "3" to the computing device 102, which then does not input the disability compensation data 126 to the disability manager engine 118. Rather, the scene rendering engine 114 may render scenes using default settings 116.

Selectable option "4" may be for replicating and/or compensating for another disability, which may not be a disability associated with the user 108, for an avatar associated with the user 108 in the virtual platform 106. For example, as depicted, option "4" is provided with selectable options 506 for selecting which disabilities may be replicated and/or compensated for, such as having "PTSD" or "Anxiety". It is understood that as selection of an option 506 does not involve PII of the user 108, no security and/or encryption may be used. In these examples, the computing device 102 may adjust the settings 116 accordingly, to replicate and/or compensate for the selected disability. For example, when an option "PTSD" is selected, the settings 116 may be adjusted such that scenes rendered by the scene rendering engine 114 have a lower brightness and/or a lower volume compared to scenes rendered using default settings 116. Similarly, when an option "Anxiety" is selected, the settings 116 may be adjusted such that a game scenes rendered by the scene rendering engine 114 may be played in a "god" mode. It is further understood that when one selectable option 506 is provided, the one selectable option 506 may be automatically selected when option "4" is selected. It is yet further understood that the computing device 102 has access to data defining how the settings 116 are to be adjusted when an option 506 is selected, and such data may be stored at the memory 128, the memory 204, and/or may be stored with the application 206.

It is further understood that, rather than providing selectable options 506, when option "4" is selected, the computing device 102 may communicate with the client device 104 to provide a questionnaire to determine which disability to replicate. For example, such a questionnaire may be provided in the form of questions and/or images, and the like, which may be answered by the user 108 and/or selected by the user 108, and such answers and/or selections may be processed by the computing device 102 to determine which disability to replicate and/or compensate for. For example, when such answers and/or selections indicate that the user 108 is tired, PTSD may be replicated and/or compensated in scenes rendered by the scene rendering engine 114, for example by adjusting the settings 116 to reduce a default volume. Similarly, when such answers and/or selections indicate that the user 108 is sad, anxiety may be replicated and/or compensated in scenes rendered by the scene rendering engine 114, for example by adjusting the settings 116 to place the virtual environment into a "god" mode, and the like.

It is further understood that the GUI 502 is optional, and that when no GUI 502 is provided, the system 100 defaults to option "1". Similarly, when the GUI 502 is provided, but no option is selected, the system 100 may default to option "1".

However, it is further understood that a GUI similar to the GUI 502 may be provided at other client devices for users who do not have a disability and/or who do not have a same disability as the user 108. For example, a user of such other client devices may want to interact with the virtual platform 106 (e.g. via a respective avatar) according to the settings 116 adjusted according to the disability compensation data 126, for example to interact with the virtual platform 106 at a reduced volume and/or using an avatar in a wheelchair, and the like. Put another way, the disability compensation data 126 may be made available to other client devices in any suitable manner (e.g. with or without a GUI) so that users associated with the other client devices may interact with the virtual platform 106 (e.g. via a respective avatar) according to the settings 116 adjusted according to the disability compensation data 126.

Figure 6:
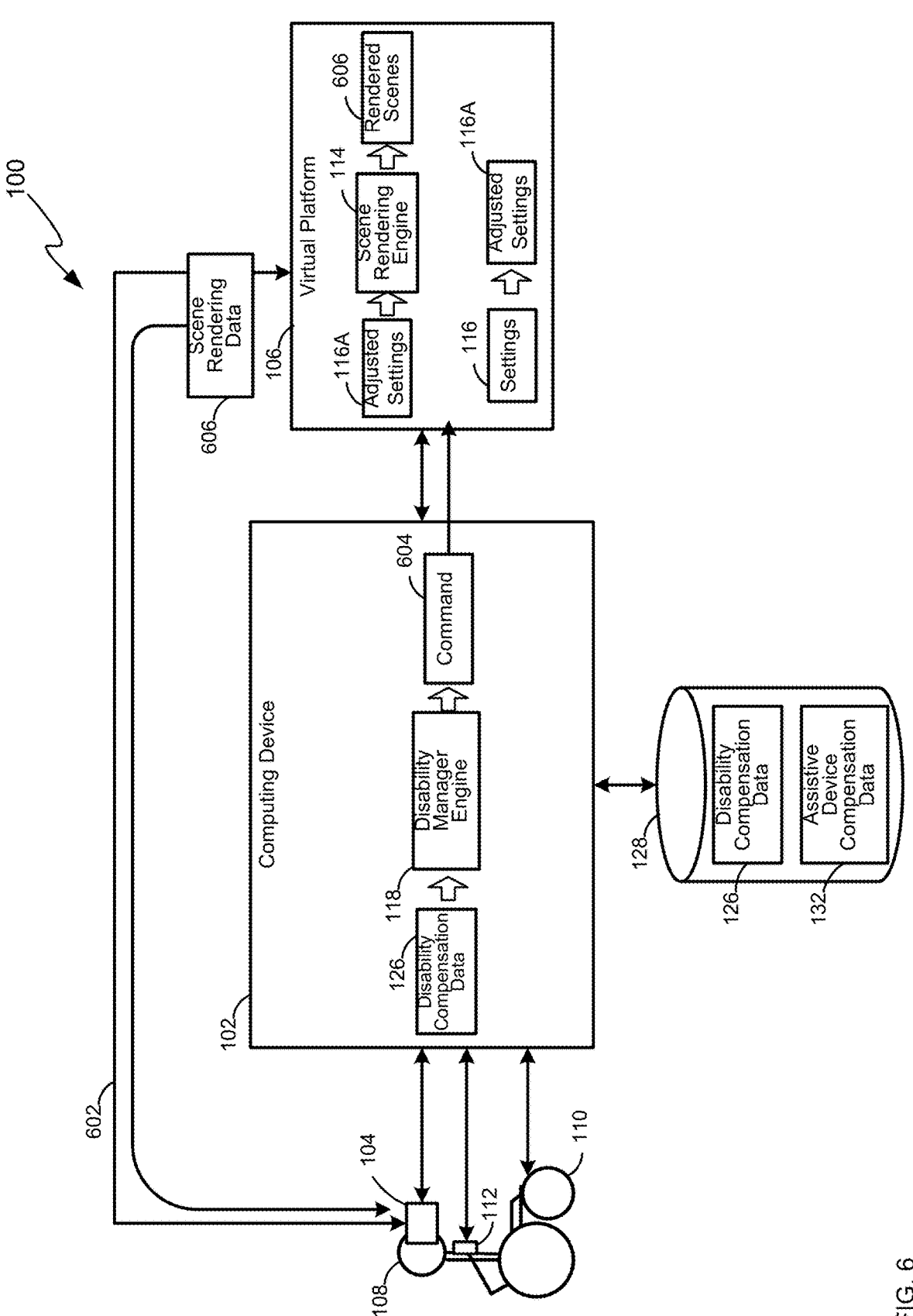
FIG. 6 depicts the system of FIG. 1 implementing yet further aspects of the method for secure access to virtual platforms, according to non-limiting examples.

Attention is next directed to FIG. 6, which depicts an example of the client device 104 establishing (e.g., at the block 302 of the method 300) a communication session 602 with the virtual platform 106, which may occur by way of the client device 104 first communicating with the computing device 102, as an intermediary, to log into the virtual platform 106. The communication session 602 is depicted as a communication link between the client device 104 and the virtual platform 106, but may occur via the computing device 102.

Furthermore, in FIG. 6, the computing device 102 is depicted as no longer having access to the memory 122 and/or the medical records 124, indicated by the memory 122 being omitted from FIG. 6. It is further understood in FIG. 6 that the copies 402 of the medical records 124 have been deleted from the computing device 102, as indicated by the copies 402 of the medical records 124 being omitted from FIG. 6.

As depicted, the computing device 102 accesses (e.g., at the block 304 of the method 300) the disability compensation data 126 at the memory 128, and input the disability compensation data 126 into the disability manager engine 118, which outputs a command 604, which may indicate adjusted settings to which the settings 116 are to be adjusted to compensate for a disability of a user 108. The command 604 may comprise such adjusted settings.

The computing device 102 further adjusts (e.g., at the block 306 of the method 300) the settings 116 of the virtual platform 106 according to the disability compensation data 126, for example by providing and/or transmitting the command 604 to the virtual platform 106, which adjusts default settings 116 to adjusted settings 116A.

For example, continuing with the above example, a default viewing height of 178 cm in the default settings 116 may be adjusted to 168 cm in the adjusted settings 116A. Similarly, a default volume of 50% cm in the default settings 116 may be adjusted to 90% in the adjusted settings 116A. Other default values of the settings 116 may not be adjusted such that corresponding values of the adjusted settings 116A may comprise such default values.

The scene rendering engine 114 uses the adjusted settings 116A to generate scene rendering data 606, which is provided to the client device 104 in the communication session 602. The scene rendering data 606 may be provided at the client device 104 as rendered scenes. The user 108 may operate the client device 104 to navigate the virtual environment represented by the scene rendering data 606, with navigation commands provided from the client device 104, to the virtual platform 106, in the communication session 602, and the scene rendering data 606 is updated accordingly, again using the adjusted settings 116A and the navigation commands.

Attention is next directed to FIG. 7, which depicts a rendered scene 702 generated with default settings 116 and a rendered scene 702 generated with the adjusted settings 116A. The rendered scene 700 is understood to be generated by the scene rendering engine 114 before the settings 116 are adjusted, and the rendered scene 702 is understood to be generated by the scene rendering engine 114 after the settings 116 are adjusted to the adjusted settings 116A. Furthermore, both of the scenes 700, 702 may represent the virtual environment of the virtual platform 106.

For example, both of the scenes 700, 702 show an avatar 704 of the user 108, and in this example the avatar 704 is in a wheelchair. In the rendered scene 700, however, a given default viewing height of the avatar 704 may be at a standing height of the avatar 704 (e.g., of 178 cm, if the avatar 704 is not in a wheelchair); hence a tree 706 is shown relative to a curb 708 as if the avatar 704 was standing and not sitting. Furthermore, a curb 708 has no ramp so the avatar 704 may not be able to move past the curb 708. Furthermore, a sounds 710 (e.g., emitted by a bird) are at a given default volume of 50%, represented by five lines of the sound 710.

In contrast, the rendered scene 702, viewing height of the avatar 704 has been adjusted to a sitting height of the avatar 704 (e.g., 168 cm); hence the tree 706 is shown in an adjusted position relative to the curb 708, as compared to the rendered scene 700. Furthermore, the curb 708 has been provided with a ramp 712 so the avatar 704 may more easily to move past the curb 708. Furthermore, the sounds 710 (e.g., emitted by a bird) have been raised from the given volume of the rendered scene 700 of 50% to 90%, as represented by the five lines of the sound 710 being changed to nine lines.

It is further understood that, in some examples, a portion of such adjustments may also be provided to other client devices associated with avatars local to the avatar 704. For example, any "physical" changes to the virtual environment, such as the ramp 712, may be provided to other client devices associated with avatars local to the avatar 704. However, changes that are particular to the avatar 704, such as the viewing height and the reduction of the sounds 710 may not be provided to other client devices associated with avatars local to the avatar 704. Put another way, any changes to "physical" components of the virtual environment, which are visible to other avatars, and/or with which other avatars may interact are provided to other client devices associated with the avatars local to the avatar 704. However, changes that only the avatar 704 may experience, such as viewing height and sound volume (e.g., and any changes to color "seen" by the avatar) may not be provided to other client devices associated with the avatars local to the avatar 704.

Figure 8:
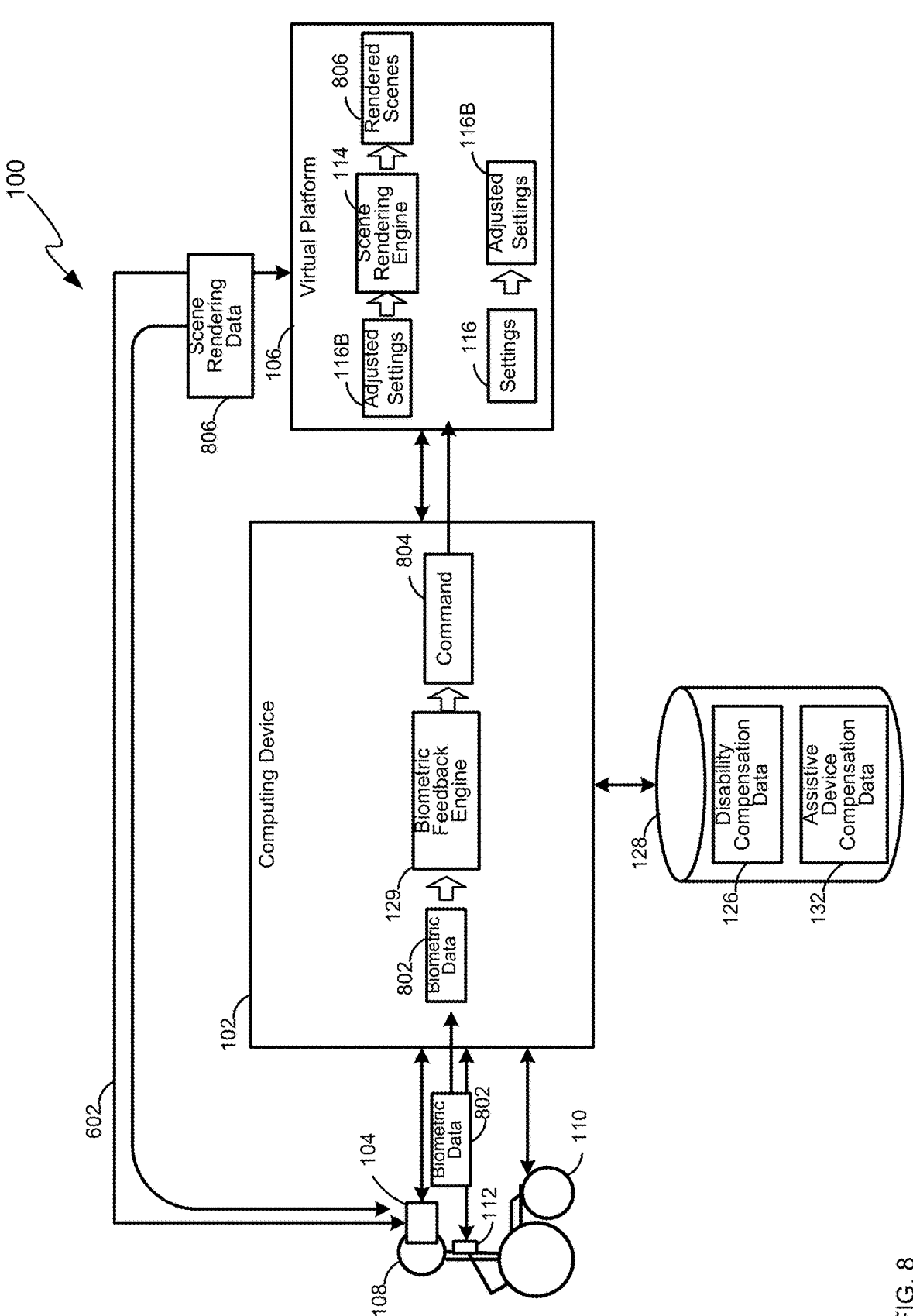
FIG. 8 depicts the system of FIG. 1 implementing yet further aspects of the method for secure access to virtual platforms, according to non-limiting examples.

Attention is next directed to FIG. 8, which depicts an example of a biometric feedback loop, which may occur during the communication session 602, and after the settings 116 are adjusted to the adjusted settings 116A. For example, as depicted, biometric data 802 is being received at the computing device 102 from the biometric device 112. The biometric data 802 is input to the biometric feedback engine 129, which outputs a command 804 (similar to the command 604) for adjusting the settings 116 (e.g., the adjusted settings 116A) based on the biometric data 802. The computing device 102 provides and/or transmits the command 804 to the virtual platform 106, which adjusts the default settings 116A to further adjusted settings 116B. The scene rendering engine 114 uses the further adjusted settings 116B to generate updated scene rendering data 806, which are provided to the client device 104 in the communication session 602. For example, in the updated scene rendering data 806 volume may be lowered from 90% to 80%, for example in an attempt to lower a heart rate of the user 108 to below a threshold heart rate.

Figure 9:
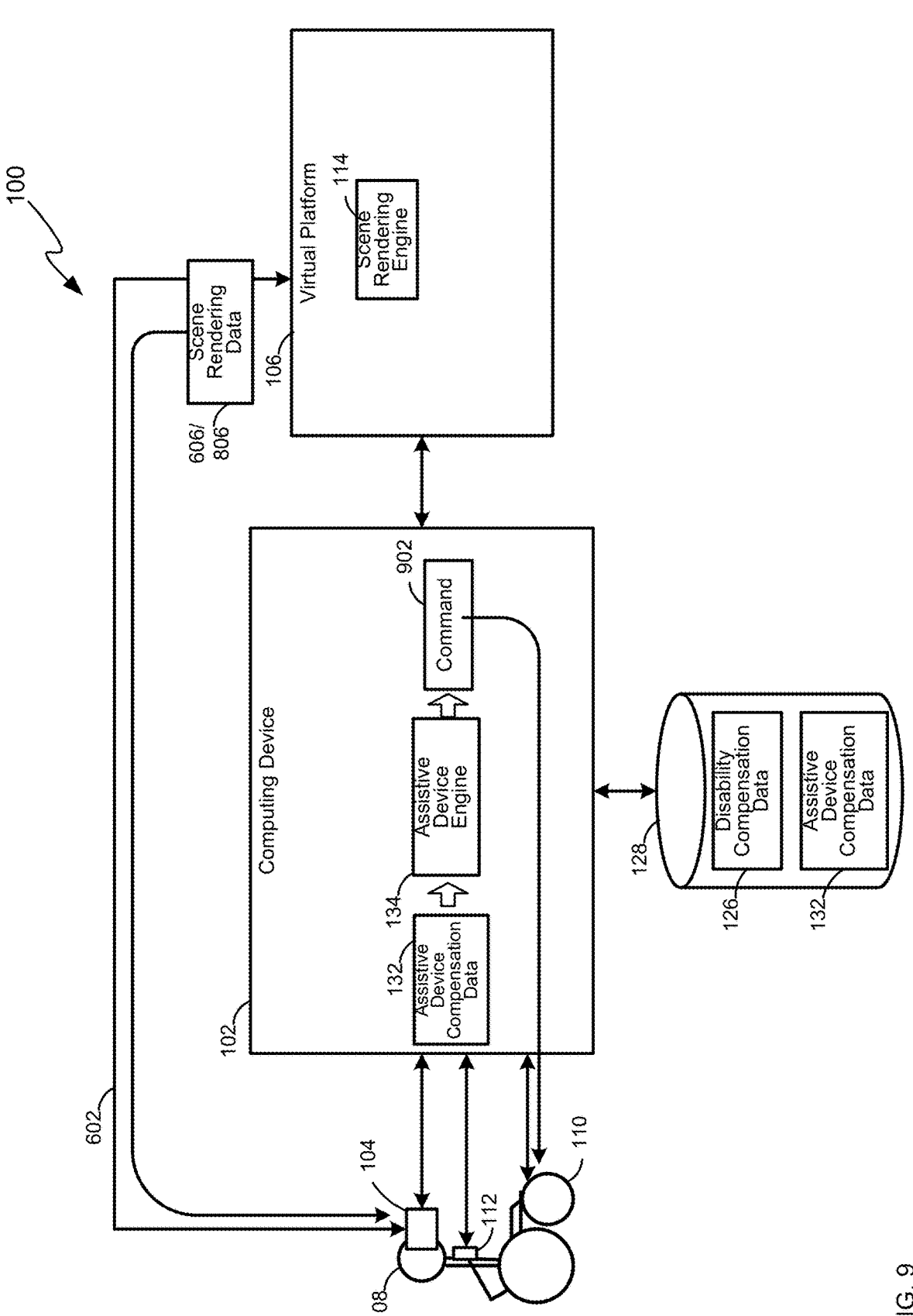
FIG. 9 depicts the system of FIG. 1 implementing yet further aspects of the method for secure access to virtual platforms, according to non-limiting examples.

Attention is next directed to FIG. 9, which depicts an example of adjusting the assistive device 110 using the assistive device compensation data 132, which may occur during the communication session 602, and after the settings 116 are adjusted to the adjusted settings 116A and/or after the adjusted settings 116A are adjusted to the further adjusted settings 116B; as such, as depicted, the virtual platform 106 may be providing any of the scene rendering data 606, 806 to the client device 104.

As depicted, the assistive device compensation data 132 is input to the assistive device engine 134, which outputs a command 902 for adjusting the assistive device 110 (e.g., to raise or lower the assistive device 110, adjust the pressure sore prevention device, and the like). The computing device 102 provides and/or transmits the command 902 to the assistive device 110, which adjusts the assistive device 110 accordingly.

While not depicted, the biometric data 802 may also be input to the assistive device engine 134 and the command 902 may adjust the assistive device 110 accordingly (for example in a feedback loop to change the biometric data 802, for example to lower blood pressure of the user 108, and the like).

As should by now be apparent, the operations and functions of the devices described herein are sufficiently complex as to require their implementation on a computer system, and cannot be performed, as a practical matter, in the human mind. In particular, computing devices, and the like, such as set forth herein are understood as requiring and providing speed and accuracy and complexity management that are not obtainable by human mental steps, in addition to the inherently digital nature of such operations (e.g., a human mind cannot interface directly with a virtual environment, control the virtual environment, adjust settings of a virtual platform based on data, amongst other features and functions set forth herein).

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is further understood that instance of the term "configured to", such as "a computing device configured to . . . ", "a processor configured to . . . ", "a controller configured to . . . ", and the like, may be understood to include a feature of a computer-readable storage medium having stored thereon program instructions that, when executed by a computing device and/or a processor and/or a controller, and the like, may cause the computing device and/or the processor and/or the controller to perform a set of operations, which may comprise the features that the computing device and/or the processor and/or the controller, and the like, are configured to implement. Hence, the term "configured to" is understood not to be unduly limiting to means plus function interpretations, and the like.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

Unless the context of usage unambiguously indicates otherwise, articles "a," "an," and "the" should not be interpreted as meaning "one" or "only one." Rather such articles should be interpreted as meaning "at least one" or "one or more." Similarly, when the terms "the" or "said" are used to refer to a noun previously introduced by the indefinite article "a" or "an," "the" and "said" mean "at least one" or "one or more" unless the usage unambiguously indicates otherwise.

The terms "about", "substantially", "essentially", "approximately", and the like, are defined as being "close to", for example as understood by persons of skill in the art. In some examples, the terms are understood to be "within 10%," in other examples, "within 5%", in yet further examples, "within 1%", in yet further examples "within 0.5%", and in yet further examples "within 0.1%".

Persons skilled in the art will appreciate that in some examples, the functionality of devices and/or methods and/or processes described herein may be implemented using pre-programmed hardware or firmware elements (e.g., application specific integrated circuits (ASICs), electrically erasable programmable read-only memories (EEPROMs), etc.), or other related components. In other examples, the functionality of the devices and/or methods and/or processes described herein may be achieved using a computing apparatus that has access to a code memory (not shown), which stores computer-readable program code for operation of the computing apparatus. The computer-readable program code could be stored on a computer readable storage medium, which is fixed, tangible and readable directly by these components, (e.g., removable diskette, CD-ROM, ROM, fixed disk, USB drive). Furthermore, it is appreciated that the computer-readable program may be stored as a computer program product comprising a computer usable medium. Further, a persistent storage device may comprise the computer readable program code. It is yet further appreciated that the computer-readable program code and/or computer usable medium may comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium may be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative examples and modifications possible, and that the above examples are only illustrations of one or more examples. The scope, therefore, is only to be limited by the claims appended hereto.

What is claimed is:

1. A method comprising:
establishing, via a computing device, a communication session between a client device and a virtual platform, the client device configured to provide rendered scenes of the virtual platform based on scene rendering data generated by the virtual platform;
accessing, via the computing device, at a memory, disability compensation data indicative of how to compensate for a disability associated with a user of the client device within virtual platforms, the disability compensation data anonymized to remove personal identifiable information associated with the user; and
adjusting, via the computing device, settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform,
wherein adjusting the settings of the virtual platform according to the disability compensation data to control the virtual platform to generate the scene rendering data according to the settings as adjusted comprises:
replicating an assistive device in the scene rendering data for the avatar, the assistive device used by the user of the client device; and
adding an accessibility feature to the scene rendering data that compensates for the assistive device of the avatar.

2. The method of claim 1, further comprising:
receiving biometric data associated with the user during the communication session; and
further adjusting the settings of the virtual platform based on the biometric data.

3. The method of claim 1, further comprising:
receiving biometric data associated with the user during the communication session; and
adjusting the disability compensation data based on the biometric data.

4. The method of claim 1, further comprising:

accessing medical records associated with the user;

generating the disability compensation data from the medical records including removing any of the personal identifiable information in the medical records from the disability compensation data; and deleting copies of the medical records generated when accessing the medical records and generating the disability compensation data.

5. The method of claim 1, wherein the disability compensation data comprises:

specific indications for adjusting the settings of the virtual platform to compensate for the disability, the specific indications including specific settings adjustments.

6. The method of claim 1, wherein the disability compensation data comprises:

generic indications for adjusting the settings of the virtual platform to compensate for the disability, the generic indications omitting specific settings adjustments, and wherein the adjusting the settings of the virtual platform according to the disability compensation data comprises:

translating the generic indications for adjusting the settings into specific setting adjustments to the settings.

7. The method of claim 1, wherein the disability compensation data omits any reference to a type of the disability.

8. The method of claim 1, further comprising:

receiving, from the client device, an indication to adjust the settings of the virtual platform; and adjusting the settings based on the indication, wherein the indication comprises one of:

a first indication to replicate, or compensate for, the disability for the avatar associated with the user in the virtual platform;

a second indication to partially replicate, or partially compensate for, the disability for the avatar in the virtual platform;

a third indication to stop replicating, or not compensate for, the disability for the avatar in the virtual platform; and a fourth indication to simulate, or compensate for, a given disability for the avatar in the virtual platform.

9. The method of claim 1, further comprising:

causing the assistive device, used by the user of the client device, to adjust, to one or more of alleviate and avoid one or more disabilities of the user of the client device in the scene rendering data generated according to the settings as adjusted.

10. A computing device comprising:

a controller; and a computer-readable storage medium having stored thereon program instructions that, when executed by the controller, cause the computing device to perform a set of operations comprising:

establishing a communication session between a client device and a virtual platform, the client device configured to provide rendered scenes of the virtual platform based on scene rendering data generated by the virtual platform;

accessing, at a memory, disability compensation data indicative of how to compensate for a disability associated with a user of the client device within virtual platforms, the disability compensation data anonymized to remove personal identifiable information associated with the user; and adjusting settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform, wherein adjusting the settings of the virtual platform according to the disability compensation data to control the virtual platform to generate the scene rendering data according to the settings as adjusted comprises:

replicating an assistive device in the scene rendering data for the avatar, the assistive device used by the user of the client device; and adding an accessibility feature to the scene rendering data that compensates for the assistive device of the avatar.

11. The computing device of claim 10, wherein the set of operations further comprises:

receiving biometric data associated with the user during the communication session; and further adjusting the settings of the virtual platform based on the biometric data.

12. The computing device of claim 10, wherein the set of operations further comprises:

receiving biometric data associated with the user during the communication session; and adjusting the disability compensation data based on the biometric data.

13. The computing device of claim 10, wherein the set of operations further comprises:

accessing medical records associated with the user;

generating the disability compensation data from the medical records including removing any of the personal identifiable information in the medical records from the disability compensation data; and deleting copies of the medical records generated when accessing the medical records and generating the disability compensation data.

14. The computing device of claim 10, wherein the disability compensation data comprises:

specific indications for adjusting the settings of the virtual platform to compensate for the disability, the specific indications including specific settings adjustments.

15. The computing device of claim 10, wherein the disability compensation data comprises:

generic indications for adjusting the settings of the virtual platform to compensate for the disability, the generic indications omitting specific settings adjustments, and wherein the adjusting the settings of the virtual platform according to the disability compensation data comprises:

translating the generic indications for adjusting the settings into specific setting adjustments to the settings.

16. The computing device of claim 10, wherein the disability compensation data omits any reference to a type of the disability.

17. The computing device of claim 10, wherein the set of operations further comprises:

receiving, from the client device, an indication to adjust the settings of the virtual platform; and adjusting the settings based on the indication, wherein the indication comprises one of:

a first indication to replicate, or compensate for, the disability for the avatar associated with the user in the virtual platform;

a second indication to partially replicate, or partially compensate for, the disability for the avatar in the virtual platform;

a third indication to stop replicating, or not compensate for, the disability for the avatar in the virtual platform; and a fourth indication to simulate, or compensate for, a given disability for the avatar in the virtual platform.

18. The computing device of claim 10, wherein the set of operations further comprises:

causing the assistive device, used by the user of the client device, to adjust, to one or more of alleviate and avoid one or more disabilities of the user of the client device in the scene rendering data generated according to the settings as adjusted.

19. A non-transitory computer-readable storage medium having stored thereon program instructions that, when executed by a computing device, causes the computing device to perform a method comprising:

establishing a communication session between a client device and a virtual platform, the client device configured to provide rendered scenes of the virtual platform based on scene rendering data generated by the virtual platform;

accessing, at a memory, disability compensation data indicative of how to compensate for a disability associated with a user of the client device within virtual platforms, the disability compensation data anonymized to remove personal identifiable information associated with the user; and adjusting settings of the virtual platform according to the disability compensation data to control the virtual platform to generate the scene rendering data according to the settings as adjusted, such that the client device renders scenes of the virtual platform according to the scene rendering data during the communication session to replicate the disability for an avatar associated with the user in the virtual platform, wherein adjusting the settings of the virtual platform according to the disability compensation data to control the virtual platform to generate the scene rendering data according to the settings as adjusted comprises:

replicating an assistive device in the scene rendering data for the avatar, the assistive device used by the user of the client device; and adding an accessibility feature to the scene rendering data that compensates for the assistive device of the avatar.

20. The non-transitory computer-readable storage medium of claim 19, wherein the method further comprises:

receiving biometric data associated with the user during the communication session; and one or more of:

further adjusting the settings of the virtual platform based on the biometric data; and adjusting the disability compensation data based on the biometric data.

* * * * *